US008889187B2

(12) United States Patent
Rudnic et al.

(10) Patent No.: US 8,889,187 B2
(45) Date of Patent: *Nov. 18, 2014

(54) ONCE A DAY AMOXICILLIN PRODUCT COMPRISING IMMEDIATE AND DELAYED RELEASE DOSAGE FORMS

(75) Inventors: Edward M Rudnic, N. Potomac, MD (US); James D Isbister, Potomac, MD (US); Donald J Treacy, Jr., Annapolis, MD (US); Sandra E Wassink, Frederick, MD (US)

(73) Assignee: Shionogi Inc., Florham Park, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 13/273,966

(22) Filed: Oct. 14, 2011

(65) Prior Publication Data

US 2012/0035121 A1 Feb. 9, 2012

Related U.S. Application Data

(63) Continuation of application No. 10/611,076, filed on Jul. 1, 2003, now abandoned, which is a continuation of application No. 10/325,780, filed on Dec. 20, 2002, now Pat. No. 6,723,341, which is a continuation of application No. 09/792,092, filed on Feb. 22, 2001, now Pat. No. 6,544,555, which is a continuation-in-part of application No. 09/687,229, filed on Oct. 13, 2000, now abandoned.

(60) Provisional application No. 60/184,546, filed on Feb. 24, 2000.

(51) Int. Cl.
| | |
|---|---|
| A61K 9/24 | (2006.01) |
| A61K 9/22 | (2006.01) |
| A61K 9/20 | (2006.01) |
| A61K 31/00 | (2006.01) |
| A61K 31/7048 | (2006.01) |
| A61K 31/43 | (2006.01) |
| A61K 31/4164 | (2006.01) |
| A61K 9/50 | (2006.01) |
| A61K 45/06 | (2006.01) |
| A61K 9/16 | (2006.01) |

(52) U.S. Cl.
CPC ............ *A61K 9/2081* (2013.01); *A61K 31/00* (2013.01); *A61K 31/7048* (2013.01); *A61K 31/43* (2013.01); *A61K 31/4164* (2013.01); *A61K 9/5084* (2013.01); *A61K 9/5026* (2013.01); *A61K 9/1652* (2013.01); *A61K 45/06* (2013.01); *A61K 9/1635* (2013.01)
USPC ............ 424/472; 424/464; 424/468; 424/471

(58) Field of Classification Search
CPC .................. A61K 9/209; A61K 9/2054
See application file for complete search history.

(56) References Cited

U.S. PATENT DOCUMENTS

| | | | |
|---|---|---|---|
| 2,809,918 | A | 10/1957 | Hermelin |
| 2,921,883 | A | 1/1960 | Reese et al. |
| 3,108,046 | A | 10/1963 | Harbit |
| 3,119,742 | A | 1/1964 | Heimlich et al. |
| 3,835,221 | A | 9/1974 | Fulberth et al. |
| 3,870,790 | A | 3/1975 | Lowey et al. |
| 4,007,174 | A | 2/1977 | Laundon |
| 4,008,246 | A | 2/1977 | Ochiai et al. |
| 4,018,918 | A | 4/1977 | Ayer et al. |
| 4,048,306 | A | 9/1977 | Maier et al. |
| 4,122,157 | A | 10/1978 | Huber |
| 4,131,672 | A | 12/1978 | Huffman |
| 4,175,125 | A | 11/1979 | Huffman |
| 4,226,849 | A | 10/1980 | Schor |
| 4,236,211 | A | 11/1980 | Arvesen |
| 4,250,166 | A | 2/1981 | Maekawa et al. |
| 4,327,725 | A | 5/1982 | Cortese et al. |
| 4,331,803 | A | 5/1982 | Watanabe et al. |
| 4,362,731 | A | 12/1982 | Hill |
| 4,369,172 | A | 1/1983 | Schor et al. |
| 4,399,151 | A | 8/1983 | Sjoerdsma et al. |
| 4,430,495 | A | 2/1984 | Patt et al. |
| 4,435,173 | A | 3/1984 | Siposs et al. |
| 4,474,768 | A | 10/1984 | Bright |
| 4,517,359 | A | 5/1985 | Kobrehel et al. |

(Continued)

FOREIGN PATENT DOCUMENTS

| | | |
|---|---|---|
| AU | 2001239869 | 12/2005 |
| AU | 2001239841 | 4/2006 |
| CA | 2251281 | 4/1999 |
| EP | 0052075 | 11/1981 |
| EP | 0222914 | 5/1987 |

(Continued)

OTHER PUBLICATIONS

Odenholt et al, Pharmacodynamic Studies of Amoxicillin Against *Streptococcus pneumoniae*: Comparison of a New Pharmacokinetically enhanced formulation (2000 mg twice daily) with standard dosage regimens, Journal of Antimicrobial Chemotherapy (2004) 54, 1062-1066.*

(Continued)

*Primary Examiner* — Carlos Azpuru
(74) *Attorney, Agent, or Firm* — MH2 Technology Law Group, LLP

(57) ABSTRACT

An antibiotic product is comprised of at least two dosages forms, each of which has a different release profile, with the $C_{max}$ for the antibiotic product being reached in less than about twelve hours. In one embodiment, there is an immediate release dosage form, as well as one or more delayed release dosage forms, with each of the dosage forms having a different release profile, wherein each reaches a $C_{max}$ at different times.

13 Claims, No Drawings

(56) References Cited

U.S. PATENT DOCUMENTS

| | | |
|---|---|---|
| 4,525,352 A | 6/1985 | Cole et al. |
| 4,529,720 A | 7/1985 | Cole et al. |
| 4,560,552 A | 12/1985 | Cole et al. |
| 4,568,741 A | 2/1986 | Livingston |
| 4,598,045 A | 7/1986 | Masover et al. |
| 4,616,008 A | 10/1986 | Hirai et al. |
| 4,634,697 A | 1/1987 | Hamashima |
| 4,644,031 A | 2/1987 | Lehmann et al. |
| 4,670,549 A | 6/1987 | Morimoto et al. |
| 4,672,109 A | 6/1987 | Watanabe et al. |
| 4,680,386 A | 7/1987 | Morimoto et al. |
| 4,710,565 A | 12/1987 | Livinston et al. |
| 4,723,958 A | 2/1988 | Pope et al. |
| 4,728,512 A | 3/1988 | Mehta et al. |
| 4,749,568 A | 6/1988 | Reusser et al. |
| 4,755,385 A | 7/1988 | Etienne et al. |
| 4,765,989 A | 8/1988 | Wong et al. |
| 4,775,751 A | 10/1988 | McShane |
| 4,794,001 A | 12/1988 | Mehta et al. |
| 4,808,411 A | 2/1989 | Lu et al. |
| 4,812,561 A | 3/1989 | Hamashima et al. |
| 4,828,836 A | 5/1989 | Elger et al. |
| 4,828,843 A | 5/1989 | Pich et al. |
| 4,831,025 A | 5/1989 | Godtfredsen et al. |
| 4,835,140 A | 5/1989 | Smith et al. |
| 4,842,866 A | 6/1989 | Horder et al. |
| 4,849,515 A | 7/1989 | Matier et al. |
| 4,879,135 A | 11/1989 | Greco et al. |
| 4,894,119 A | 1/1990 | Baron, Jr. et al. |
| 4,895,934 A | 1/1990 | Matier et al. |
| 4,904,476 A | 2/1990 | Mehta et al. |
| 4,915,953 A | 4/1990 | Jordan et al. |
| 4,933,186 A | 6/1990 | Ohm et al. |
| 4,938,967 A | 7/1990 | Newton et al. |
| 4,945,080 A | 7/1990 | Lindstrom et al. |
| 4,945,405 A | 7/1990 | Hirota |
| 4,971,805 A | 11/1990 | Kitanishi et al. |
| 4,981,468 A | 1/1991 | Benefiel et al. |
| 4,990,602 A | 2/1991 | Morimoto et al. |
| 5,007,790 A | 4/1991 | Shell |
| 5,011,692 A | 4/1991 | Fujioka et al. |
| 5,045,533 A | 9/1991 | Phillippe et al. |
| 5,051,262 A | 9/1991 | Panoz et al. |
| 5,110,597 A | 5/1992 | Wong et al. |
| 5,110,598 A | 5/1992 | Kwan et al. |
| 5,143,661 A | 9/1992 | Lawter et al. |
| 5,158,777 A | 10/1992 | Abramowitz et al. |
| 5,178,874 A | 1/1993 | Kwan et al. |
| 5,182,374 A | 1/1993 | Tobkes et al. |
| 5,200,193 A | 4/1993 | Radebaugh et al. |
| 5,204,055 A | 4/1993 | Sachs et al. |
| 5,213,808 A | 5/1993 | Bar-Shalom et al. |
| 5,229,131 A | 7/1993 | Amidon et al. |
| 5,230,703 A | 7/1993 | Alon |
| 5,260,068 A | 11/1993 | Chen |
| 5,260,069 A | 11/1993 | Chen |
| 5,274,085 A | 12/1993 | Amano et al. |
| 5,288,503 A | 2/1994 | Wood et al. |
| 5,326,570 A | 7/1994 | Rudnic et al. |
| 5,334,590 A | 8/1994 | DiNinno et al. |
| 5,340,656 A | 8/1994 | Sachs et al. |
| 5,358,713 A | 10/1994 | Shimamura |
| 5,387,380 A | 2/1995 | Cima et al. |
| 5,393,765 A | 2/1995 | Infeld et al. |
| 5,395,626 A | 3/1995 | Kotwal et al. |
| 5,395,628 A | 3/1995 | Noda et al. |
| 5,399,723 A | 3/1995 | Iinuma et al. |
| 5,401,512 A | 3/1995 | Rhodes et al. |
| 5,413,777 A | 5/1995 | Sheth et al. |
| 5,414,014 A | 5/1995 | Schneider et al. |
| 5,422,343 A | 6/1995 | Yamamoto et al. |
| 5,430,021 A | 7/1995 | Rudnic et al. |
| 5,445,829 A | 8/1995 | Pradissis et al. |
| 5,457,187 A | 10/1995 | Gmeimer et al. |
| 5,462,747 A | 10/1995 | Radebaugh et al. |
| 5,466,446 A | 11/1995 | Stiefel et al. |
| 5,472,708 A | 12/1995 | Chen |
| 5,476,854 A | 12/1995 | Young |
| 5,490,962 A | 2/1996 | Cima et al. |
| 5,508,040 A | 4/1996 | Chen |
| 5,518,680 A | 5/1996 | Cima et al. |
| 5,538,954 A | 7/1996 | Koch et al. |
| 5,543,417 A | 8/1996 | Waldstreicher |
| 5,556,839 A | 9/1996 | Greene et al. |
| 5,567,441 A | 10/1996 | Chen |
| 5,576,022 A | 11/1996 | Yang et al. |
| 5,578,713 A | 11/1996 | McGill, III |
| 5,599,557 A | 2/1997 | Johnson et al. |
| 5,607,685 A | 3/1997 | Cimbollek et al. |
| 5,633,006 A | 5/1997 | Catania et al. |
| 5,635,613 A | 6/1997 | Greene et al. |
| 5,672,359 A | 9/1997 | Digenis et al. |
| 5,688,516 A | 11/1997 | Raad et al. |
| 5,702,895 A | 12/1997 | Matsunaga et al. |
| 5,705,190 A | 1/1998 | Broad et al. |
| 5,707,646 A | 1/1998 | Yajima et al. |
| 5,719,132 A | 2/1998 | Lin et al. |
| 5,719,272 A | 2/1998 | Yang et al. |
| 5,725,553 A | 3/1998 | Moenning |
| 5,733,886 A | 3/1998 | Baroody et al. |
| 5,756,473 A | 5/1998 | Liu et al. |
| 5,780,446 A | 7/1998 | Ramu |
| 5,789,584 A | 8/1998 | Christensen et al. |
| 5,808,017 A | 9/1998 | Chang |
| 5,817,321 A | 10/1998 | Alakhov et al. |
| 5,827,531 A | 10/1998 | Morrison et al. |
| 5,837,284 A | 11/1998 | Mehta et al. |
| 5,837,829 A | 11/1998 | Ku |
| 5,840,329 A | 11/1998 | Bai |
| 5,840,760 A | 11/1998 | Carraher, Jr. et al. |
| 5,844,105 A | 12/1998 | Liu et al. |
| 5,849,776 A | 12/1998 | Czernielewski et al. |
| 5,852,180 A | 12/1998 | Patel |
| 5,858,986 A | 1/1999 | Liu et al. |
| 5,864,023 A | 1/1999 | Ku et al. |
| 5,869,170 A | 2/1999 | Cima et al. |
| 5,872,104 A | 2/1999 | Vermeulen et al. |
| 5,872,229 A | 2/1999 | Liu et al. |
| 5,877,243 A | 3/1999 | Sarangapani |
| 5,883,079 A | 3/1999 | Zopf et al. |
| 5,892,008 A | 4/1999 | Ku et al. |
| 5,910,322 A | 6/1999 | Rivett et al. |
| 5,919,219 A | 7/1999 | Knowlton |
| 5,919,489 A | 7/1999 | Saleki-Gerhardt et al. |
| 5,919,916 A | 7/1999 | Gracey et al. |
| 5,929,219 A | 7/1999 | Hill |
| 5,932,710 A | 8/1999 | Liu et al. |
| 5,945,124 A | 8/1999 | Sachs et al. |
| 5,945,405 A | 8/1999 | Spanton et al. |
| 5,948,440 A | 9/1999 | Arora et al. |
| 5,972,373 A | 10/1999 | Yajima et al. |
| 5,972,389 A | 10/1999 | Shell et al. |
| 5,980,942 A | 11/1999 | Katzhendler et al. |
| 5,985,643 A | 11/1999 | Tomasz et al. |
| 5,998,194 A | 12/1999 | Summers, Jr. et al. |
| 6,008,195 A | 12/1999 | Selsted |
| 6,010,718 A | 1/2000 | Al-Razzak et al. |
| 6,013,507 A | 1/2000 | Tomasz et al. |
| 6,027,748 A | 2/2000 | Conte et al. |
| 6,031,093 A | 2/2000 | Cole et al. |
| 6,048,977 A | 4/2000 | Cole et al. |
| 6,051,255 A | 4/2000 | Conley et al. |
| 6,051,703 A | 4/2000 | Cole et al. |
| 6,057,291 A | 5/2000 | Hancock et al. |
| 6,059,816 A | 5/2000 | Moenning |
| 6,063,613 A | 5/2000 | De Lencastre et al. |
| 6,063,917 A | 5/2000 | Ascher et al. |
| 6,068,859 A | 5/2000 | Curatolo et al. |
| 6,110,498 A | 8/2000 | Rudnic et al. |
| 6,110,925 A | 8/2000 | Williams et al. |
| 6,117,843 A | 9/2000 | Baroody et al. |
| 6,120,803 A | 9/2000 | Wong et al. |
| 6,127,349 A | 10/2000 | Chasalow |
| 6,132,768 A | 10/2000 | Sachs et al. |

(56) References Cited

U.S. PATENT DOCUMENTS

| | | |
|---|---|---|
| 6,132,771 A | 10/2000 | Depui et al. |
| 6,136,345 A | 10/2000 | Grimmett et al. |
| 6,136,587 A | 10/2000 | Tomasz et al. |
| 6,156,507 A | 12/2000 | Hiramatsu et al. |
| 6,159,491 A | 12/2000 | Durrani |
| 6,162,925 A | 12/2000 | Williams et al. |
| 6,183,778 B1 | 2/2001 | Conte et al. |
| 6,187,768 B1 | 2/2001 | Welle et al. |
| 6,214,359 B1 | 4/2001 | Bax |
| 6,218,380 B1 | 4/2001 | Cole et al. |
| 6,228,398 B1 | 5/2001 | Devane et al. |
| 6,231,875 B1 | 5/2001 | Sun et al. |
| 6,241,526 B1 | 6/2001 | Auran et al. |
| 6,248,363 B1 | 6/2001 | Patel et al. |
| 6,251,647 B1 | 6/2001 | De Lencastre et al. |
| 6,265,394 B1 | 7/2001 | Sterzycki et al. |
| 6,270,805 B1 | 8/2001 | Chen et al. |
| 6,280,771 B1 | 8/2001 | Monkhouse et al. |
| 6,294,199 B1 | 9/2001 | Conley et al. |
| 6,294,526 B1 | 9/2001 | Higuchi et al. |
| 6,296,873 B1 | 10/2001 | Katzhendler et al. |
| 6,297,215 B1 | 10/2001 | Hancock et al. |
| 6,299,903 B1 | 10/2001 | Rivett et al. |
| 6,306,436 B1 | 10/2001 | Chungi et al. |
| 6,309,663 B1 | 10/2001 | Patel et al. |
| 6,322,819 B1 | 11/2001 | Burnside et al. |
| 6,326,027 B1 | 12/2001 | Miller et al. |
| 6,333,050 B2 | 12/2001 | Wong et al. |
| 6,340,475 B2 | 1/2002 | Shell et al. |
| 6,352,720 B1 | 3/2002 | Martin et al. |
| 6,358,525 B1 | 3/2002 | Guo et al. |
| 6,358,528 B1 | 3/2002 | Grimmett et al. |
| 6,361,797 B1 | 3/2002 | Kuzma et al. |
| 6,375,988 B1 | 4/2002 | Suzuki et al. |
| 6,376,967 B2 | 4/2002 | Saamaa et al. |
| 6,383,471 B1 | 5/2002 | Chen et al. |
| 6,384,081 B2 | 5/2002 | Berman |
| 6,391,614 B1 | 5/2002 | Tomasz et al. |
| 6,399,086 B1 | 6/2002 | Katzhendler et al. |
| 6,403,569 B1 | 6/2002 | Achterrath |
| 6,406,717 B2 | 6/2002 | Cherukuri |
| 6,406,880 B1 | 6/2002 | Thornton |
| 6,440,462 B1 | 8/2002 | Raneburger et al. |
| 6,444,796 B1 | 9/2002 | Suh et al. |
| 6,468,964 B1 | 10/2002 | Rowe |
| 6,479,496 B1 | 11/2002 | Wolff |
| 6,495,157 B1 | 12/2002 | Pena et al. |
| 6,497,901 B1 | 12/2002 | Royer |
| 6,503,709 B1 | 1/2003 | Bekkaoui et al. |
| 6,506,886 B1 | 1/2003 | Lee et al. |
| 6,514,518 B2 | 2/2003 | Monkhouse et al. |
| 6,515,010 B1 | 2/2003 | Franchini et al. |
| 6,515,116 B2 | 2/2003 | Suh et al. |
| 6,530,958 B1 | 3/2003 | Cima et al. |
| 6,541,014 B2 | 4/2003 | Rudnic et al. |
| 6,544,555 B2 | 4/2003 | Rudnic et al. |
| 6,548,083 B1 | 4/2003 | Wong et al. |
| 6,550,955 B2 | 4/2003 | D'Silva |
| 6,551,584 B2 | 4/2003 | Bandyopadhyay et al. |
| 6,551,616 B1 | 4/2003 | Notario et al. |
| 6,558,699 B2 | 5/2003 | Venkatesh |
| 6,565,873 B1 | 5/2003 | Shefer et al. |
| 6,565,882 B2 | 5/2003 | Rudnic |
| 6,569,463 B2 | 5/2003 | Patel et al. |
| 6,585,997 B2 | 7/2003 | Moro et al. |
| 6,599,884 B2 | 7/2003 | Avrutov et al. |
| 6,605,069 B1 | 8/2003 | Albers et al. |
| 6,605,300 B1 | 8/2003 | Burnside et al. |
| 6,605,609 B2 | 8/2003 | Barbachyn et al. |
| 6,605,751 B1 | 8/2003 | Gibbins et al. |
| 6,610,323 B1 | 8/2003 | Lundberg et al. |
| 6,610,328 B2 | 8/2003 | Rudnic et al. |
| 6,617,436 B2 | 9/2003 | Avrutov et al. |
| 6,623,757 B2 | 9/2003 | Rudnic et al. |
| 6,623,758 B2 | 9/2003 | Rudnic et al. |
| 6,624,292 B2 | 9/2003 | Lifshitz et al. |
| 6,627,222 B2 | 9/2003 | Rudnic et al. |
| 6,627,743 B1 | 9/2003 | Liu et al. |
| 6,630,498 B2 | 10/2003 | Gudipati et al. |
| 6,632,451 B2 | 10/2003 | Penhasi et al. |
| 6,632,453 B2 | 10/2003 | Rudnic et al. |
| 6,635,280 B2 | 10/2003 | Shell et al. |
| 6,638,532 B2 | 10/2003 | Rudnic et al. |
| 6,642,276 B2 | 11/2003 | Wadhwa |
| 6,663,890 B2 | 12/2003 | Rudnic et al. |
| 6,663,891 B2 | 12/2003 | Rudnic et al. |
| 6,667,042 B2 | 12/2003 | Rudnic et al. |
| 6,667,057 B2 | 12/2003 | Rudnic et al. |
| 6,669,948 B2 | 12/2003 | Rudnic et al. |
| 6,669,954 B2 | 12/2003 | Crison et al. |
| 6,669,955 B2 | 12/2003 | Chungi et al. |
| 6,673,369 B2 | 1/2004 | Rampal et al. |
| 6,682,759 B2 | 1/2004 | Lim et al. |
| 6,696,426 B2 | 2/2004 | Singh et al. |
| 6,702,803 B2 | 3/2004 | Kupperblatt et al. |
| 6,706,273 B1 | 3/2004 | Roessler |
| 6,723,340 B2 | 4/2004 | Gusler et al. |
| 6,723,341 B2 | 4/2004 | Rudnic et al. |
| 6,730,320 B2 | 5/2004 | Rudnic et al. |
| 6,730,325 B2 | 5/2004 | Devane et al. |
| 6,735,470 B2 | 5/2004 | Henley et al. |
| 6,740,664 B2 | 5/2004 | Cagle et al. |
| 6,746,692 B2 | 6/2004 | Conley et al. |
| 6,747,014 B2 | 6/2004 | Teng et al. |
| 6,756,057 B2 | 6/2004 | Storm et al. |
| 6,767,899 B1 | 7/2004 | Kay et al. |
| 6,777,420 B2 | 8/2004 | Zhi et al. |
| 6,783,773 B1 | 8/2004 | Storm et al. |
| 6,797,283 B1 | 9/2004 | Edgren et al. |
| 6,814,979 B2 | 11/2004 | Rudnic et al. |
| 6,818,407 B2 | 11/2004 | Hancock et al. |
| 6,824,792 B2 | 11/2004 | Foreman et al. |
| 6,838,093 B2 | 1/2005 | Flanner et al. |
| 6,872,407 B2 | 3/2005 | Notario et al. |
| 6,878,387 B1 | 4/2005 | Petereit et al. |
| 6,881,420 B2 | 4/2005 | Flashner-Barak et al. |
| 6,906,035 B2 | 6/2005 | Hancock et al. |
| 6,913,768 B2 | 7/2005 | Couch et al. |
| 6,916,801 B2 | 7/2005 | Buynak et al. |
| 6,929,804 B2 | 8/2005 | Rudnic et al. |
| 6,932,981 B2 | 8/2005 | Sen et al. |
| 6,946,458 B2 | 9/2005 | Turos |
| 6,984,401 B2 | 1/2006 | Rudnic et al. |
| 6,991,807 B2 | 1/2006 | Rudnic et al. |
| 7,008,633 B2 | 3/2006 | Yang et al. |
| 7,025,989 B2 | 4/2006 | Rudnic et al. |
| 7,074,417 B2 | 7/2006 | Rudnic et al. |
| 7,105,174 B2 | 9/2006 | Rudnic et al. |
| 7,108,859 B2 | 9/2006 | Rudnic et al. |
| 7,122,204 B2 | 10/2006 | Rudnic et al. |
| 7,157,095 B2 | 1/2007 | Rudnic et al. |
| 2001/0008756 A1 | 7/2001 | Auran et al. |
| 2001/0046984 A1 | 11/2001 | Rudnic et al. |
| 2001/0048944 A1 | 12/2001 | Rudnic et al. |
| 2002/0004070 A1 | 1/2002 | Rudnic et al. |
| 2002/0004499 A1 | 1/2002 | Rudnic et al. |
| 2002/0015728 A1 | 2/2002 | Payumo et al. |
| 2002/0028920 A1 | 3/2002 | Lifshitz et al. |
| 2002/0042394 A1 | 4/2002 | Hogenkamp et al. |
| 2002/0068078 A1 | 6/2002 | Rudnic et al. |
| 2002/0068085 A1 | 6/2002 | Rudnic et al. |
| 2002/0081332 A1 | 6/2002 | Rampal et al. |
| 2002/0103181 A1 | 8/2002 | Sen et al. |
| 2002/0103261 A1 | 8/2002 | Ninkov |
| 2002/0106412 A1 | 8/2002 | Rowe et al. |
| 2002/0115624 A1 | 8/2002 | Behar et al. |
| 2002/0119168 A1 | 8/2002 | Rudnic et al. |
| 2002/0136764 A1 | 9/2002 | Rudnic et al. |
| 2002/0136765 A1 | 9/2002 | Rudnic et al. |
| 2002/0136766 A1 | 9/2002 | Rudnic et al. |
| 2002/0150619 A1 | 10/2002 | Rudnic et al. |
| 2002/0197314 A1 | 12/2002 | Rudnic et al. |
| 2003/0012814 A1 | 1/2003 | Rudnic et al. |
| 2003/0018295 A1 | 1/2003 | Henley et al. |

(56) References Cited

U.S. PATENT DOCUMENTS

| | | |
|---|---|---|
| 2003/0049311 A1 | 3/2003 | McAllister et al. |
| 2003/0064100 A1 | 4/2003 | Rudnic et al. |
| 2003/0073647 A1 | 4/2003 | Chao et al. |
| 2003/0073648 A1 | 4/2003 | Chao et al. |
| 2003/0073826 A1 | 4/2003 | Chao et al. |
| 2003/0077323 A1 | 4/2003 | Rudnic et al. |
| 2003/0086969 A1 | 5/2003 | Rudnic et al. |
| 2003/0091627 A1 | 5/2003 | Sharma |
| 2003/0092696 A1 | 5/2003 | Buynak et al. |
| 2003/0096006 A1 | 5/2003 | Rudnic et al. |
| 2003/0096007 A1 | 5/2003 | Rudnic et al. |
| 2003/0096008 A1 | 5/2003 | Rudnic et al. |
| 2003/0099706 A1 | 5/2003 | Rudnic et al. |
| 2003/0099707 A1 | 5/2003 | Rudnic et al. |
| 2003/0104054 A1 | 6/2003 | Rudnic et al. |
| 2003/0104055 A1 | 6/2003 | Rudnic et al. |
| 2003/0104056 A1 | 6/2003 | Rudnic et al. |
| 2003/0104058 A1 | 6/2003 | Rudnic et al. |
| 2003/0124196 A1 | 7/2003 | Weinbach et al. |
| 2003/0129236 A1 | 7/2003 | Heimlich et al. |
| 2003/0143268 A1 | 7/2003 | Pryce Lewis et al. |
| 2003/0147953 A1 | 8/2003 | Rudnic et al. |
| 2003/0190360 A1 | 10/2003 | Baichwal et al. |
| 2003/0198677 A1 | 10/2003 | Pryce Lewis et al. |
| 2003/0199808 A1 | 10/2003 | Henley et al. |
| 2003/0203023 A1 | 10/2003 | Rudnic et al. |
| 2003/0206951 A1 | 11/2003 | Rudnic et al. |
| 2003/0216555 A1 | 11/2003 | Lifshitz et al. |
| 2003/0216556 A1 | 11/2003 | Avrutov et al. |
| 2003/0232089 A1 | 12/2003 | Singh et al. |
| 2003/0235615 A1 | 12/2003 | Rudnic |
| 2004/0018234 A1 | 1/2004 | Rudnic et al. |
| 2004/0033262 A1 | 2/2004 | Kshirsagar et al. |
| 2004/0043073 A1 | 3/2004 | Chen et al. |
| 2004/0047906 A1 | 3/2004 | Percel et al. |
| 2004/0048234 A1 | 3/2004 | Vanderbist et al. |
| 2004/0052842 A1 | 3/2004 | Rudnic et al. |
| 2004/0058879 A1 | 3/2004 | Avrutov et al. |
| 2004/0091528 A1 | 5/2004 | Rogers et al. |
| 2004/0096496 A1 | 5/2004 | Kshirsagar et al. |
| 2004/0126427 A1 | 7/2004 | Venkatesh et al. |
| 2004/0176737 A1 | 9/2004 | Henley et al. |
| 2004/0219223 A1 | 11/2004 | Kunz |
| 2004/0253249 A1 | 12/2004 | Rudnic et al. |
| 2004/0265379 A1 | 12/2004 | Conley et al. |
| 2005/0019401 A1 | 1/2005 | Burnside et al. |
| 2005/0019402 A1 | 1/2005 | Burnside et al. |
| 2005/0019403 A1 | 1/2005 | Burnside et al. |
| 2005/0031685 A1 | 2/2005 | Sen et al. |
| 2005/0037071 A1 | 2/2005 | Cao et al. |
| 2005/0037076 A1 | 2/2005 | Burnside et al. |
| 2005/0048114 A1 | 3/2005 | Burnside et al. |
| 2005/0053658 A1 | 3/2005 | Venkatesh et al. |
| 2005/0058708 A1 | 3/2005 | Burnside et al. |
| 2005/0064033 A1 | 3/2005 | Notario et al. |
| 2005/0064034 A1 | 3/2005 | Li et al. |
| 2005/0142187 A1 | 6/2005 | Treacy et al. |
| 2005/0163857 A1 | 7/2005 | Rampal et al. |
| 2005/0203076 A1 | 9/2005 | Li et al. |
| 2005/0203085 A1 | 9/2005 | Li et al. |
| 2005/0209210 A1 | 9/2005 | Ding et al. |
| 2005/0238714 A1 | 10/2005 | Rudnic et al. |
| 2005/0256096 A1 | 11/2005 | Combrink et al. |
| 2005/0261262 A1 | 11/2005 | Ma et al. |
| 2005/0277633 A1 | 12/2005 | Ma et al. |
| 2006/0003005 A1 | 1/2006 | Cao et al. |
| 2006/0019985 A1 | 1/2006 | Ma et al. |
| 2006/0019986 A1 | 1/2006 | Ding et al. |
| 2006/0099253 A1 | 5/2006 | Becker et al. |
| 2006/0110455 A1 | 5/2006 | Rudnic et al. |
| 2006/0111302 A1 | 5/2006 | Romsberg et al. |
| 2006/0193908 A1 | 8/2006 | Burnside et al. |
| 2006/0222705 A1 | 10/2006 | Flanner et al. |
| 2007/0134327 A1 | 6/2007 | Flanner et al. |
| 2007/0154547 A1 | 7/2007 | Flanner et al. |

FOREIGN PATENT DOCUMENTS

| | | |
|---|---|---|
| EP | 0293885 | 12/1988 |
| EP | 0436370 | 7/1991 |
| EP | 0652008 | 5/1995 |
| EP | 0752850 | 1/2002 |
| FR | 2585947 | 2/1982 |
| FR | 2585948 | 2/1982 |
| GB | 2087235 | 5/1982 |
| WO | 90/08537 | 8/1990 |
| WO | 94/27557 | 12/1994 |
| WO | 95/20946 | 8/1995 |
| WO | 95/28148 | * 10/1995 |
| WO | 95/30422 | 11/1995 |
| WO | 96/04908 | * 2/1996 |
| WO | 97/22335 | 6/1997 |
| WO | 97/43277 | 11/1997 |
| WO | 98/22091 | 5/1998 |
| WO | 98/46239 | 10/1998 |
| WO | 99/03453 | 1/1999 |
| WO | 99/40097 | 8/1999 |
| WO | 00/48607 | 8/2000 |
| WO | 00/61116 | 10/2000 |
| WO | 01/26663 | 4/2001 |
| WO | 01/62195 | 8/2001 |
| WO | 01/62229 | 8/2001 |
| WO | 01/62231 | 8/2001 |
| WO | 02/38577 | 5/2002 |
| WO | 02/41876 | 5/2002 |
| WO | 03/029439 | 4/2003 |
| WO | 03/066064 | 8/2003 |
| WO | 03/075852 | 9/2003 |
| WO | 03/086344 | 10/2003 |
| WO | 2004/012509 | 2/2004 |
| WO | 2004/012704 | 2/2004 |
| WO | 2004/012713 | 2/2004 |
| WO | 2004/012717 | 2/2004 |
| WO | 2004/812509 | 2/2004 |
| WO | 2004/089299 | 10/2004 |
| WO | 2004/103311 | 12/2004 |
| WO | 2005/009364 | 2/2005 |
| WO | 2005/009365 | 2/2005 |
| WO | 2005/009368 | 2/2005 |
| WO | 2005/016278 | 2/2005 |
| WO | 2005/016311 | 2/2005 |
| WO | 2005/023184 | 3/2005 |
| WO | 2005/027877 | 3/2005 |
| WO | 2005/056754 | 6/2005 |
| WO | 2005/062898 | 7/2005 |
| WO | 2005/070941 | 8/2005 |
| WO | 2006/014427 | 2/2006 |
| WO | 2006/105350 | 10/2006 |
| WO | 2007/006770 | 6/2007 |
| WO | 2007/079082 | 7/2007 |
| WO | 2008/142627 | 11/2008 |

OTHER PUBLICATIONS

United States Code Annotated, 21 U.S.C, § 379(g), effective Oct. 1, 2002.

Eagle et al., Effect of Schedule of Administration on the Therapeudic Efficacy of Penicillin, American Journal of Medicine, Sep. 1950, pp. 280-299.

Adjei et al., Comparative Pharmacokinetic Study of Continuous Venous Infusion Fluorouracil and Oral Fluorouracil With Eniluracli in Patients with Advanced Solid Tumors, Journal of Clinical Oncology, vol. 20, Issue 6 Mar. 2002, 1686-1691.

Andes, Pharmacokinetic and Pharmacodynamic Properties of Antimicrobials in the Therapy of Respiratory Tract Infections, Current Opinion in Infectious Diseases, 14(2):165-172, Apr. 2001 (Abstract).

Auckenthaler, Pharmacokinetics and Pharmacodynamics of Oral Beta-Lactam Antibiotics as a Two-Dimensional Approach to Their Efficacy, J. Antimicrob Chemother, (2002) 50, 13-17.

Bahnmuller, Metabolites of Microorganisms, 248. Synthetic Analogs of Saphenamycin, J. Antibiot (Tokyo). Nov. 1988; 41(11); 1552-60.

Berry et al., Bacteriological Efficacies of Three Macrolides Compared with Those Amoxicillin-Clavulanate Against *Streptococcus*

(56) References Cited

OTHER PUBLICATIONS

*pneumoniae* and *Haemophilus influenzae*, Antimicrob Agents Chemother. Dec. 1998, 42(12): 3193-3199.
Bhargava et al., Pulsed Feeding During Fed-Batch Fungal Fermentation Leads to Reduced Viscosity Without Detrimentally Affecting Protein Expression, Biotechnology and Bioengineering, vol. 81, No. 3, Feb. 5, 2003, pp. 341-347.
Bhargava et al., Pulsed Feeding During Fed-Bath *Aspergillus oryzae* Fermentation Leads to Improved Oxygen Mass Transfer, Biotechnol. Prog, 2003, 19, 1091-1094.
Bhargava et al., Pulsed Addition of Limiting-Carbon During *Aspergillus oryzae* Fermentation Leads to Improved Productivity of a Recombinant Enzyme, Biotechnology and Bioengineering, vol. 82, No. 1, Apr. 5, 2003, pp. 111-117.
Borman, Chemistry Highlights 2005, Chemical & Engineering News, Dec. 19, 2005, vol. 83, No. 51, pp. 15-20.
Bradley, *Staphylococcus aureus* Pneumonia: Emergence of MRSA in the Community, Semin Respir Crit Care Med. 2005; 26(6): 643-649.
Brogden et al., Cefixime. A Review of Its Antibacterial Activity, Pharmacokinetic Properties and Therapeutic Potential, Drugs; Oct. 1989; 38(4): 524-50. (Abstract).
Brunton et al. Acute Otitis Media, Supplement to the Journal of Family Practice, Nov. 2005, pp. 961-968.
Byfield et al., Relevance of the Pharmacology of Oral Tegafur to its Use as a 5-FU Pro-Drug., Cancer Treat Rep. Jun. 1985; 69(6): 645-52. (Abstract).
Cappelletty et al., Bactericidal Activities of Cefprozil, Penicillin, Cefaclor, Cefixime, and Loracarbef against Penicillin-Susceptible and -Resistant *Streptococcus pneumoniae* in an in Vitro Pharmacodynamic Infection Model, Antimicrobial Agents and Chemotherapy, May 1996, pp. 1148-1152.
Cha et al., Pulsatile Delivery of Amoxicillin Against *Streptococcus pneumoniae*, Journal of Antimicrobial Chemotherapy, Advance Access Published Oct. 14, 2004.
Chawia et al., Gastroretention a Means to Address Regional Variability in intestinal Drug Absorption, Pharmaceutical Technology, Jul. 2003, pp. 50-68.
Chen, An Alternative Approach for Assessment of Rate of Absorption in Bioequivalence Studies, Pharmaceutical Research, vol. 9, No. 11, 1992, pp. 1380-1385.
Cirz et al., Inhibition of Mutation and Combating the Evolution of Antibiotic Resistance, PLOS Biology, Jun. 2005, vol. 3, Issue 6, e176. pp. 1024-1033.
Craig, Antibiotic Selection Factors and Description of a Hospital-Based Outpatient Antibiotic Therapy Program in the USA, Eur J Clin Microbiol Infect Dis. Jul. 1995; 14(7): 636-42. (Abstract).
Craig, Antimicrobial Resistance Issues of the Future, Diagn Microbiol Infect Dis. Aug. 1996; 25(4): 213-7. (Abstract).
Cremieux et al., Ceftriaxone Diffusion into Cardiac Fibrin Vegetation. Qualitative and Quantitative Evaluation by Autoradiography, Fundam Clin Pharmacol. 1991; 5(1):53-60. (Abstract).
Darst, New Inhibitors Targeting Bacterial RNA Polymerase, Trends in Biochemical Sciences, vol. 29, No. 4, Apr. 2004, pp. 159-162.
Dellit, M.D., Tim et al., Interim Guidelines or Evaluation and Management of Community-Associated Methicillin-Resistant *Staphylococcus aureus* Skin and Soft Tissue Infections in Outpatient Settings, Sep. 2, 2004.
Endo et al., Fungicidal Action of Aureobasidin A, a Cyclic Depsipeptide Antifungal Antibiotic, against *Saccharomyces cerevisiae*, Antimicrobial Agents and Chemotherapy, Mar. 1997, pp. 672-676.
Erah et al., The Stability of Amoxicillin, Charithromycin and Metronidazole in Gastric Juice: Relevance to the Treatment of *Helicobacter pylori* Infection, J Antimicrob Chemother Jan. 1997; 39(1): 5-12.
Feder et al., Once-Daily Therapy for Streptococcal Pharyngitis With Amoxicillin, American Academy of Pediatrics, vol. 103(1), Jan. 1999, pp. 47-51.

Freeman et al., The Cyclosporin-Erythromycin Interaction: Impaired First Pass Metabolism in the Prg, Br J Pharmacol. Jul. 1991; 103(3): 1709-12. (Abstract).
Frimodt-Moller, Correlation Between Pharmacokinetic / Pharmacodynamic Parameters and Efficacy for Antibiotics in the Treatment of Urinary Tract Infection, Int. J. Antimicrob. Agents, 19 (2002) 546-53.
Furianut et al., Pharmacokinetic Aspects of Levofloxacin 500mg Once Daily During Sequential Intravenous/Oral Therapy in Patients with Lower Respiratory Tract Infections, Journal of Antimicrobial Chemotherapy (2003) 51, 101-106.
Geiger et al., Metabolites of Microorganisms, 247. Phenazines from Streptomyces Antibioticus , Strain Tu 2706, J. Antibiot (Tokyo). Nov. 1988; 41(11): 1542-51.
Gill et al., In Vivo Activity and Pharmacokinetic Evaluation of a Novel Long-Acting Carbapenem Antibiotic, MK-826 (L-749, 345), Antimicrobial Agents and Chemotherapy, Aug. 1998: 42(8): 1996-2001.
Gordon et al., Rationale for Single and High Dose Treatment Regiments with Azithromycin, Pediatric Infectious Disease Journal, 23(2) Supplement: S102-S107, Feb. 2004. (Abstract).
Gorwitz et al., Strategies for Clinical Management of MRSA in the Community: Summary of an Expert's Meeting Convened by the Centers for Disease Control and Prevention, Department of Health and Human Services Centers for Disease Control and Prevention, Mar. 2006.
Goswick et al., Activities of Azithromycin and Amphotericin B Against *Naegelria fowlein* in Vitro and in a Mouse Model of Primary Amebic Resistance, Circulation Jun. 27, 2000; 101:2916-2921.
Harbarth et al., Prolonged Antibiotic Prophylaxis After Cardiovascular Surgery and Its Effect on Surgical Site Infections and Antimicrobial Resistance, Circulation Jun. 27, 2000; 101:2916-2921.
Haney, New Drugs Kill Bacteria to Antibiotics, Called Ketolides. They are Chemically New to the Harmful Bugs, Thursday, Sep. 21, 2000, Seattle Post-Intelligencer.
Henry, Disabling Resistance Inhibiting Key Protease Prevents Bacteria from Evolving Drug Resistance, Chemical and Engineering News, May 16, 2005, vol. 83, No. 20, p. 8.
Hickey et al., Production of Enterolysis A by a Raw Milk Enterococcal Isolate Exhibiting Multiple Virulence Factors, Microbiology 149 (2003), 655-664.
Hilton et al., Use of Hydroxypropyl Methylcellulose Acetate Succinate in an Enteric Polymer Matrix to Design Controlled-Release Tablets of Amoxicillin Trihydrate, Journal of Pharmaceutical Sciences, vol. 82, No. 7, Jul. 1993, pp. 737-743.
Hirata et al., Pharmacokinetic Study of S-1, a Novel Oral Fluorouracil Antitumor Drug, Clinical Cancer Research, vol. 5, 2000-2005, Aug. 1999.
Hoff et al., Phase I Study of Pharmacokinetic of S-1 on an Oral Daily Schedule for 28 Days in Patients with Solid Tumors, Clinical Cancer Research, vol. 9, 134-142, Jan. 2003.
Hoffman et al., Pharmacodynamic and Pharmacokinetic Rationales for the Development of an Oral Controlled-Released Amoxicillin Dosage Form, Journal of Controlled Release 54 (1998) 29-37.
Hoffman et al., Influence of Macrolide Susceptibility on Efficacies of Clarithromycin and Azithromycin Against *Streptococcus pneumoniae* in a Murine Lung Infection Model, Antimicrobial Agents and Chemotherapy, Feb. 2003, p. 739-746, vol. 47, No. 2.
Hyde et al., Macrolide Resistance Among Invasive *Streptococcus penumoniae* Isolates, JAMA, Oct. 17, 2001; 286(15): 1857-62. (Abstract).
Iba et al., Comparison Between Continuous Intravenous and Oral Administration of 5-FU with LV, Gan To Kagaku Ryoho, Apr. 1999: 26(5): 631-5. (Abstract).
Johnson, N.J., Experts Urge Prudent Antibiotic Use, Exaimer.Com, The Associated Press, Jul. 31, 2006.
Kaplan et al., Macrolide Therapy of Group A *Streptococcus* Pharyngitis: 10 Days of Macrolide Therapy (Clarithromycin) is More Effective in Streptococcal Eradication Than 5 Days (Azithromycin), Clin Infect Dis. Jun. 15, 2001; 32(12): 1798-802, Epub May 21, 2001. (Abstract).
Kitahara et al., Saphenamycin, A Novel Antibiotic From a Strain of *Streptomyces*, J Antibiot (Tokyo). Oct. 1982; 35 (10); 1412-4.

(56) References Cited

OTHER PUBLICATIONS

Klugman, Bacteriological Evidence of Antibiotic Failure in Penumococcal Lower Respiratory Tract Infections, Eur Respir J 2002; 20 Suppl. 36, 3s-8s.

Kramar et al., Statistical Optimization of Diclofenac Release Pellets Costed with Polymethacrylic Films, Int J. Pharm. Apr. 30, 2003: 256(1-2): 43-52. (Abstract).

Laine et al., Frequency and Clinical Outcome of Potentially Harmful Drug Metabolic Interactions in Patients Hospitalized on Internal Pulmonary Medicine Wards: Focus on Warfarin and Cisapride, Therapeutic Drug Monitoring. 22(5):503-509, Oct. 2000. (Abstract).

Laine et al., Frequency and Clinical Outcome of Potentially Harmful Drug Metabolic Interactions in Patients Hospitalized on Internal Pulmonary Medicine Wards: Focus on Warfarin and Cisapride, Therapeutic Drug Monitoring. 22(5):503-509, Oct. 2000.

Lamb et al., Ceftriaxone: An Update of its Use in the Management of Community-Acquired and Noscocomial Infections, Drugs. 2002; 62(7) 1041-89. (Abstract).

Laursen et al., Solid-Phase Synthesis of New Saphenamycin Analogues with Antimicrobial Activity, Bioorg. Med. Chem. Lett. Jan. 21, 2002; 12(2):171-5.

Laursen et al., First Synthesis of Racemic Saphenamycin and Its Enantiomers. Investigation of Biological Activity, Bioorg. Med. Chem. Mar. 6, 2003; 11(5):723-31.

Laursen et al., Efficient Synthesis of Glycosylated Phenazine Natural Products and Analogs with DISAL (Methyl 3, 5-Dinitrosalicylate) Glycosyl Donors, Org. Biomol. Chem. Sep. 21, 2003; 1(18):3147-53.

Lemer-Tung et al., Pharmacokinetics of Intrapericardial Administration of 5-Fluorouracil, Cancer Chemother Pharmacol. 1997; 40(4):318-20. (Abstract).

Lin et al., Multiple-Dose Pharmacokinetics of Ceftibuten in Healthy Volunteers, Antimicrobial Agents and Chemotherapy, Feb. 1995, pp. 356-358.

Lind et al., Eradication of *Helicobacter pylori* using one-week triple therapies combining omeprazole with two antimicrobials: the MACH I Study, Helicobater, Sep. 1996: 1(3);138-44. (Abstract).

Lindsey et al., Extraction of Antibiotics From Agricultural Wastewater, USGS, 220th ACS Meeting, Washington, D.C., Aug. 20-24, 2000. (Abstract).

Livermore et al., Activity of Ertapenem Against *Neisseria gonorrhea*, Journal of Antimicrobial Chemotherapy 2004 54 (1): 280-281.

Lovmar et al., Kinetics of Macrolide Action, The Josamycin and Erythromycin Cases, J Biol. Chem., vol. 279, Issue 51, 53506-53515, Dec. 17, 2004.

Mainz et al., Pharmacokinetics of Lansoprazole, Amoxicillin and Clarithromycin After Simultaneous and Single Administration, Journal of Antimicrobial Chemotherapy (2002) 50, 699-706.

Marten et al., Monthly Report, Jul. 2004, Pulsatile Dosing of Antifungal Compounds, UMBC; to Dr. Robert J. Guttendorf, Advancis Pharmaceutical Corp.

Mazzei, et al., How Macrolide Pharmacodynamics Affect Bacterial Killing. Infect Med 16(sE):22-28, 1999. (Abstract).

Nightingale, Pharmacokinetics of Newer Macrolides, Pediatric Infectious Disease Journal, 16(4):438-443, Apr. 1997. (Abstract).

Olofinlade et al., Anal Carcinoma: A 15-Year Retrospective Analysis, Scand J Gastroenterol 2000:35; 1194-1199.

Pacifico et al., Comparative Efficacy and Safety of 3-Day Azithromycin and 10-Day Penicillin V Treatment of Group A Beta-Hemolytic Stretptococcal Pharyngitis in Children, Antimicrobial Agents in Chemotherapy, Apr. 1996, 1005-1008, vol. 40, No. 4. (Abstract).

Parmar-Lapasia et al., A Comparison of Two Macrolide Antibiotics in the Treatment of Community-Acquired Infections, P & T (Pharmacy & Therapeutics), Oct. 2003, vol. 28, No. 10.

Peters et al., Fouorouracil (5FU) Pharmacokinetics in 5FU Prodrug Formulations with a Dihydropyrimidine Dehydrogenase Inhibitor, Journal of Clinical Oncology, vol. 19, Issue 22 Nov. 15, 2001: 4267-4269.

Polak, Pharmacokinetics of Amphotericin B and Flucytosine, Postgrad Med J. Sep. 1979: 55(647):667-70. (Abstract).

Pichichero, Acute otitis meida: making sense of recent guidelines on antimicrobial treatment; several new recommendations could influence treatment choices, Journal of Family Practice, Apr. 1, 2005.

Pichichero et al., Controversies in the Medical Management of Persistent and Recurrent Acute Otitis Media, Recommendations of a Clinical Advisory Committee, Ann Otol Rhinol Laryngol 109:2000, pp. 2-12.

Porter et al., Antibiotics and Infectious Diseases in Otolaryngology—HNS, Grand Rounds Presentation, UTMB, Dept. of Otolaryngology, May 8, 2002.

Ramminger et al., Transittion-Metal Catalyzed Synthesis of Ketoprofen, J. Braz. Chem, Soc. vol. 11, No. 2, 105-111, 2000.

Ramu, Compounds and Methods that Reduce the Risk of Extravasation Injury Associated with the Use of Vesicant Antineoplastic Agents, Baylor College of Medicine, Aug. 6, 1998.

Ranga Rao et al., Influence of Molecular Size and Water Solubility of the Solute on its Release from Swelling and Erosion Controlled Polymeric Matrices, Journal of Controlled Release, 12 (1990) 133-141.

Reusser, Inhibition of Ribosomal and RNA Polymerase Functions by Rubradirin and Its Aglycone, J. Antibiot (Tokyo), Nov. 1979; 32(11):1186-92.

Reza et al., Comparative Evaluation of Plastic, Hydrophobic and Hydrophilic Polymers as Matrices for Controlled-Release Drug Delivery, J. Pharm Pharmaceutical Sci, 6(2):282-291, 2003.

Richardson, The Discovery and Profile of Fluconazole, J. Chemother. Feb. 1990: 2(1):51-4 (Abstract) and Houang et al., Fluconazole Levels in Plasma and Vaginal Secretions of Patients After a 150-Milligram Single Oral Dose and Rate of Eradication of Infection in Vaginal Candidiasis, Antimicrob Agents Chemother. May 1990; 34(5): 909-10. (Abstract).

Rihn, et al., Community-Acquired Methicillin-Resistant *Staphylococcus aureus*: An Emerging Problem in the Athletic Population, AM J Sports Med. Dec. 2005, 33(12): 1924-9.

Rivkees et al., Dexamethasone Treatment of Virilizing Congenital Adrenal Hyperplasia: The Ability to Achieve Normal Growth, Pediatrics 2000:106; 767-773.

Roblin et al., In Vitro Activity of a New Ketolide Antibiotic, HMR 3647, Against *Chlamydia penumoniae*, Antimicrob Agents Chemother. Jun. 1998: 42(6): 1515-1516.

Rybak, Declaration of Michael J. Rybak, In the United States Patent and Trademark Office, Applicant(s): Rudnic et al., U.S. Appl. No. 09/792,092, filed Feb. 22, 2001; executed Sep. 23. 2002.

Salmenlinna et al., Community-Acquired Methicillin-Resistant *Staphylococcus aureus*, Finland, Emerg. Infect. Dis. Jun. 2002; 8(6):602-7.

Salmenlinna et al., Community-Acquired Methicillin-Resistant *Staphylococcus aureus*, Finland, Emerging Infectious Diseases, vol. 8, No. 6, Jun. 2002, pp. 602-604.

Sandip et al., Controlled Release Formulation of Tramadol Hydrochloride Using Hydrophillic and Hydrophobic Matrix System, AAPS PharmSciTech 20031 4(3) Article 31.

Santinie et al., The Potential of Amifostine: From Cytoprotextant to Therapeutic Agent, Haematologica Nov. 1999; 84(ii):1035-1042.

Sanz et al., Cefepime Plus Amikacin Versus Piperacillin-Tazobactam Plus Amikacin for Initial Antibiotic Therapy in Hematology Patients with Febrile Neutropenia: Results of an Open, Randomized, Multicentre Trial, Journal of Antimicrobial Chemotherapy (2002) 50, 79-88.

Schaad et al., Azithromycin Versus Penicillin V for Treatment of Acute Group A Streptococcal Pharyngitis, The Pediatric Infectious Disease Journal: vol. 21(4) Apr. 2002, pp. 304-308.

Schoemaker et al., Estimating potency for the E-max model without attaining maximal effects, J. Pharmacokinet Biophar. Oct. 26, 1998(5): 581-93. (Abstract).

Schutze et al., Duodenal ulcer healing after 7-day treatment: a pilot study with lansoprazole, amoxicillin and clarithromycin; Z Gastroentrol. 1995 No.; 33(11):651-3. (Abstract).

Schutze et al., Duodenal ulcer healing after 7-day treatment: a pilot study with lansoprazole, amoxicillin and clarithromycin, Z Gastroentrol. Nov. 1995; 33(11);651-3.

Schweizer et al., "Single Shot" Prevention in Abdominal Surgery. Antibiotics with Long Half-Line (Cefriaxone, Omidazole) vs. Anti-

(56) References Cited

OTHER PUBLICATIONS biotics with Short Half-Life (Cefazolin, Metronidazole, Clindamycin), Helv Chir Acta. Apr. 1994; 60 (4):483-8. (Abstract).
Shvartzman et al., Treatment of Streptococcal Pharyngitis with Amoxycillin Once a Day. BMJ vol. 306, pp. 1170-1172. May 1, 1993.
Sica et al., The Antihypertensive Efficacy and Safety of a Chronotherapeutic Formulation of Propanolol in Patients with Hypertension, J Clin Hypertens 6(5):231-241, 2004. (Absstract).
Sica et al., Pharmacologic and Therapeutic Considerations in Considerations in Hypertension Therapy with Calcium Channel Blockers; Focus on Verapamil, J Clin Hypertens 9(2):Feb. 1-22, 2007. (Abstract).
Suda et al., The Synthesis and in Vitro and in Vitro Stability of 5-Fluorouracil Prodrugs which Possess Serum Albumin binding Potency, Biol Pharm Bull. Sep. 1993; 16(9):876-8. (Abstract).
Therlot, Mechanics of Cell Division, Mar. 2, 1998, pp. 1-12.
Todar's Online Textbook of Bacteriology, Antimicrobial Agents Used in Treatment of Infectious Disease, 2002, Kenneth Todar University of Wisconsin-Madison Department of Bacteriology.
Vandenesch et al., Community-Acquired Methicillin-Resistant *Staphylococcus aureus* Carrying Penton-Valentine Leukocidin Genes: Worldwide Emergence, Emerg. Infect. Dis. Aug. 2003;9(8):978-84.
Vanderkooi et al., Antimicrobial Resistance and the Pneumococcus, Infectious Diseases and Microbiology, vol. 3, Issue 5, May 2004.
Villalobos et al., Pharmacokinetics and Pharmacodynamics of Antibacterial Agents in Pediatrics: A Practical Approach, Jacksonville Medicine, Aug. 1998.
Waters, Colorectal Cancer-Drug Treatment, Hospital Pharmacist, vol. 11, pp. 179-192, May 2004.
Wattenberg, Prevention of Carcinogenesis of the Respiratory Tract by Chemopreventive Agents Delivered by Aeorosol, International Society of Cancer Chemoprevention, vol. 1, No. 5, Jan. 2003.
Whitehead et al., Amoxycillin Release From a Floating Dosage Form Based on Alginates, International Journal of Pharmaceutics 210 (2000) 45-49.
Advancis Pharmaceutical Corp, Jun. 15, 2005 Press Release, Advancis Pharmaceutical Announces Results from Adult / Adolescent Amoxicillin PULSYS Phase III Trial.
Advancis Pharmaceutical Corp., Jul. 21, 2005 Press Release, Advancis Pharmaceutical Announces Results from Pediatric Amoxicillin PULSYS Phase III Trial.
Advancis Pharmaceutical Corp., Mar. 29, 2005 Press Release, Advancis Pharmaceutical Completes Enrollment in Adult / Adolescent Amoxicillin PULSYS Phase III Trial.
Akaike information criterion p. 1-2, Apr. 10, 2006.
Augmentin XR, AX:L9, Prescribing Information, GlaxoSmithKline Dec. 2006.
Antibiotics Turn Profits in a Preweaning Program, Pfizer Salud Animal pp. 1-9, Pfizer 2007.
Augmentin XR (PDR entry for) (GlaxoSmithKline), (Amoxicillin/Clavulanate Potassium), Extended Release Tablets, Jun. 2004.
Can We Prevent Bacteria From Developing Resistance to Antibiotics?, Sep. 2005, AAPS News Magazine 15.
Citizen Petition, McNeil Comsumer & Specialty Pharmaceuticals, Mar. 19, 2004.
Clarithromycin Extended-Release Scientific Posters Presented to the 39th Interscience Conference on Antimicrobial Agents and Chernotheraphy (ICAAC), San Francisco, Sep. 26-29, 1999.
Clearance and the Elimination Rate Constant, Ke (Elimination Rate)—Half-Life, Oct. 14, 2002.
ClinicalTrials.gov, APC-111 Tablet Once a Day vs. Penicillin VK Four Times a Day Both for 10 Days in Patients With Strep Throat, Identifier NCT00242281, May 11, 2007.
ClinicalTrials,gov, APC-111 Once a Day (QD) for 7 Days vs. Penicillin Taken Four Times a Day (QID) for 10 Days in Patients With Strep Throat, Identifier NCT00095358, May 11, 2007.
ClinicalTrials.gov, APC-231 Once a Day (QD) for 7 Days vs. Penicillin Taken Four Times a Day (QID) in Pediatric Patients with Strep Throat, Identifier NCT0010012, May 11, 2007.

Declaration of Michael J. Ryback from the prosecution history of U.S. Appl. No. 09/792,092; Sep. 23, 2002.
Declaration of Akaike's Information Criterion, About Inc. 2006, pp. 1-2.
Dispension Errors With Depakote, New Formulation Creates Confusion, Patient Safety, Practitioners Reporting News, USP Issued Mar. 3, 2001.
Elimination Rate Constant/Half-Like, Ke (Elimination Rate)—Half Life, Oct. 14, 2002.
Fabrication of Metronidazole Strips, 996 Die Pharmazie 50 Feb. 1995. No. 2.
Five vs. 10 Days of Therapy for Treptococcal Pharyngitis, American Family Physician, Feb. 15, 2001.
Guidance for Industry, Bioavailability and Bioequivalence Studies for Orally Administered Drug Products—General Considerations, U.S. Department of Health and Human Services Food and Drug Administration Center for Drug Evaluation and Research (CDER) Mar. 2003 BP Revision 1.
Healthcare-Associated Methicillin Resistant *Staphylococcus aureus* (HA-MRSA), Department of Health and Human Services, Centers for Disease Control and Prevention, Jun. 1, 2005.
Highlights on Antineoplastic Drugs, Pharmacia, vol. 11, No. 4, 1993.
Klarithran, Ranbaxy (SA)(PTY) LTD, Jun. 2005.
MedicineNet.com, Generic Name: Acyclovir, Brand Name: Zovirax, Dec. 31, 1997.
The Merck Index, An Encyclopedia of Chemicals, Drugs, and Biologicals, Twelfth Edition, pp. 397-398 (1996).
Methicillin-Resistant *Staphylococcus aureus*, HealthLink, Medical College of Wisconsin, Information Provided by the Wisconsin Department of Health and Family Services, Article Reviewed: Apr. 10, 2000, 2003 Medical College of Wisconsin.
Methicillin-Resistant *Staphylococcus aureus* (MRSA) Infection, Written by Dr. Alan Johnson, Clinical Scientist, Website: www.mrsasupport.co.uk, Aug. 1, 2005.
Methods of Formulating Controlled Release Products Outside of the Claims of Forest Laboratory Patents U.S. 4,369,172 and U.S. 4,389,393, Technical Information, Dow Chemical, Feb. 1991.
Mode of Action of Macrolides in Blocking Translation During Bacterial Protein Synthesis: Blocking Peptidyltransferase. Doc Kaiser's Microbiology Home Page, Oct. 13, 2004.
Module 8—Therapeutics May 25, 2002. Newcastle., BPAIIG Immunology/Infectious Diseases Training Programme, Module: Therapeutics.
*Neisseria meningitis*, The Doctor's Doctor, Nov. 8, 2004.
New-Generation Aromatase Inhibitor for Breast Cancer: Anastrozole Challenges Tamoxifen in First-Line Therapy, 10th European Cancer Conference (ECCO 10), Vienna, Austria/Sep. 12-16, 1999.
New Product Newswire, Drug Topics Archive, Aug. 5, 2002.
Nitrofurantoin, Eckered Prescription Advisory, Feb. 15, 2001.
Nursing, Cancer Nursing: Principles and Practice, Fifth Edition, Jones and Barlett Publishers, 2000.
Oral Capecitabine Should Improve Convenience of Chemoradiation for Locally Advanced Rectal Cancer—New Treatment Appears to be Safe and Effective, PeerView Press, Chemotherapy (ICAAC), Sep. 27-30, 2002: San Diego, CA., 40th Annual Meeting of Infectious Diseases Society.
Pharmaceuticals, Pharmacos Unit F2 Pharmaceuticals V 6.0, Eudralex Collection 3AQ19a 1992.
Physicians Desk Reference, PDR 57 Edition 2003, p. 402/Abbott.
Procardia XL (Nifedipine) Extended Release Tablets for Oral Use, 69-4467-00-8, Pfizer Labs, Aug. 2003.
The Public's Health, Back-To-School: Review Immunization Records Early, What Doctors and Parents Need to Know About Immunizations and School, vol. 5, No. 7, Jul.-Aug. 2005.
Sustained or Differential Release Type, USPTO Classification Definitions (Dec. 2002 Edition) 964.
Testicular Cancer: Questions and Answers, Cancer Facts, National Cancer Institute, Aug. 14, 2003.
Traditional Chemotherapy, Chapter 25 from Prevention and Therapy of Cancer and Other Common Disease: Alternative and Traditional Approaches; Infomedix 1996.

(56) References Cited

OTHER PUBLICATIONS

Bisno et al., Practice Guidelines for the Diagnosis and Management of Group A Streptococcal Pharyngitis, CID 2002: 35 (Jul. 15) 113-125.

Clegg et al., Treatment of Streptococcal Pharyngitis With Once-Daily With Twice-Daily Amoxicillin, A Noninferiority Trial, The Pediatric Infectious Disease Journal, vol. 25, No. 9, Sep. 2006, pp. 761-767.

Erah et al., The Stability of amoxycillin, clarithromycin and metronidazole in gastric juice: relevance to the treatment of *Helibacter pylori* infection; Jan. 1997; Journal of Antimicrob. Chemother. 39(1):5-12. PMID: 9044021 (Abstract Only).

Yousef et al., Combined action of amoxycillin and dicloxicillin aganst *Staphylococcus aureus* in vitro; Sep. 1985; Pharmazie; 40(9): 650-1 PMID: 3877939 (Abstract Only)/.

Gnarpe et al., Penicillin combinations against multi-resistant urinary pathogens as an alternative to gentamycin treatment; 1976; Microbios.: 16(65-66):201-6 PMID: 18651 (Abstract Only).

Bishai, Comparative Effectiveness of Different Macrolides: Clarithromycin, Azithromycin, and Erythromycin, Johns Hopkins Point of Care Information Technology (POC-IT), 2001.

Burgess et al., A Time-Kill Evaluation of Clarithromycin and Azithromycin Against Two Extracellular Pathogens and the Development of Resistance, The Annals of Pharmacotherapy: (2002) vol. 33, No. 12, pp. 1262-1265 (Abstract).

Fang, A Study of the Ethical Considerations and Implications, Prozac Weekly and Sarafem In the Wake of Prozac, Patent Expiration, 5.22J/10,02J, Biotechnology and Engineering, 2002.

Harris et al., Esophageal Carcinoma: Curative Treatment, Combined Modalities, The Virtual Hospital, 2004.

Jacobs, Pharmacodynamic Approach to Antimicrobial Treatment for Respiratory Infections, Department of Pathology, Case Western Reserve University, 2006.

Janssen, Properties of Immobilised Penicillin G Acylase in β-Lactam Antibiotic Synthesis, 2006.

Stringer et al., Section 3: Diseases of the Ear, Part 4: Inner Ear, Chapter 46: Ototoxicity, Paparella: vol. II, Otology and Neuro-Otology, 1990.

About Macrolides, About That Bug.com, 2006.

Amoxycillin (As Trihydrate), Moxyvit, 2003.

Amoxycillin+Clavulanante, PetPlace.com, 2005.

Answers.com, Macrolide, 2006.

Oral Extended (Controlled) Release Dosage Forms, In Vivo Bioequivalence and In Vitro Dissolution Testing, Office of Generic Drugs, 1993.

Antimetabolites, GPnotebook, 2005.

ATRIPLA, NDA 21-937, pp. 4-53, 2006.

Augmentin, Product Information, GlaxeSmithKline, Physicians Desk References, Jun. 2004, pp. 1421-1433.

Beta Lactam Antibiotics, Health 24.com, 2005.

Biaxin XL, Once-Daily Biaxin XL Clarithromycin Extended-Release Tablets, Abbot Laboratories Online, 2004.

Biaxin XL, Once-daily, Abbott, 2004.

Biaxin Filmtab, Biaxin XL Filmtab, Biaxin Granules, pp. 1-25, Abbott Laboratories, 2005.

Body Chemistry, Acid Alkaline Foods, Acid Reflux? Gas, Acid Indigestion, Acid/Alkaline Balance, Printed from timberwave.com/chemistry.html on Jan. 2, 2012.

ClinicalTrials.gov, Search results for Advancis [All Fields], May 11, 2007.

Code of Federal Regulations, 21 CFR §§ 320.23-320.24, Apr. 23, 2006.

Cross-Reference Art Collections, 901-907: Aug. 2003.

Drugs.com, Drug Information for Diclofenac (Topical), 2006.

Encyclopedia Britannica Online, Types of Drugs>Antimicrobial Drugs>Antibiotics>Macrolides, Mar. 28, 2006.

Excenel, Swine Health Management, Prewean Program. Pfizer Salud Animal, 2005.

Food and Drug Administration Center for Drug Evaluation and Research Approved Drug Products With Therapeutic Equivalence Evaluations, 24th Edition, Feb. 26, 2004.

Food and Drug Administration Center for Drug Evaluation and Research Approved Drug Products With Therapeutic Equivalence Evaluations, 27th Edition, Jan. 29, 2007.

Klucel Hydroxypropylcellulose (HPC). Hercules Incorporated, 2004.

Meeting the Challenge of a New Generation of Respiratory Pathogens, MAC, 2001.

The Merck Index, An Encyclopedia of Chemicals, Drugs, and Biologicals, Twelfth Edition, 1996, pp. 397-398.

Clotrimazole, The Merck Index, Monograph No. 02442, 2005.

Monistat, Which Treatment is Right for You?, Vaginal vs. Oral Therapy, 2004.

Summary of Product Characteristics, Doxycycline Capsules BP 50 mg, Nov. 2001.

Complementary Medicine Saves Money, Medicine, Greenhealthwatch.com, Collection of medical headlines citing to sources dated between May 1, 1997 and Aug. 10, 2002.

Drug, Bio-Affecting and Body Treating Compositions Sustained or differential release, U.S. Patent Classification System—Classification Definitions as of Jun. 30, 2000.

Emulsions, Secundum Artem, vol. 4, No. 1, printed from www.padocklabs.com/html/resource/pdf/sed Artem4.1.pdf on Jan. 2, 2012.

Gefting a Drug Into the Body: Absorption from How Drugs Work: Basic Pharmacology for Healthcare Professionals, Hugh McGarock, 2nd Edition, May 2005.

Jock Itch and Other dermatophytes. Mycolog.com (Sep. 2002).

Miconazole, The Merck Index Results—Form View, Monograph No. 06202, 2005.

Principles of Diagnosis of Infectious Diseases and Antimicrobial Therapy, Antibiotic Guideline, Dr. Norman Miller et al., 2nd Edition, Chapters 1-3, printed from www.sassit.co.za/Journal/Infections/Antibiotics/Middes/AntibioticGuide/pdf printed on Jan. 2, 2012.

Sulfonamide Class Antibiotics, ChemicalLand21.com, printed from ChemicalLand21/info/sulfonamideclassantibiotics.html on Jan. 2, 2012.

Summary of Product Characteristics, Doxycycline Capsules BP 50mg, Nov. 2001.

Sustained-Release Dosage Forms, Degussa. Rohm Pharma Polymers printed from www.solimide.eu/en/pharmapolymers/service/literature/practical_course. Par. 0001.TRow.0010.TCell.0003.File, tmp/pc_30_sutained.pdf on Jan. 2, 2012.

* cited by examiner

ONCE A DAY AMOXICILLIN PRODUCT COMPRISING IMMEDIATE AND DELAYED RELEASE DOSAGE FORMS

This application is a continuation of U.S. patent application Ser. No. 10/611,076, filed Jul. 1, 2003 (now abandoned), which is a continuation of U.S. application Ser. No. 10/325,780, filed on Dec. 20, 2002 (now U.S. Pat. No. 6,723,341), which application is a continuation of U.S. application Ser. No. 09/792,082, filed on Feb. 22, 2001(now U.S. Pat. No. 6,544,555), which is a continuation-in-part of U.S. application Ser. No. 09/687,229, filed on Oct. 13, 2000 (abandoned), and also claims the priority of U.S. Provisional Application Ser. No. 60/184,546 filed on Feb. 24, 2000. The disclosures of each of the above-mentioned applications are hereby incorporated by reference in their entireties.

This invention relates to an antibiotic product, as well as the use and formulation thereof.

A wide variety of antibiotics have been used, and will be used, in order to combat bacterial infection. In general, such antibiotics can be administered by a repeated dosing of immediate release dosage forms, which results in poor compliance or as a controlled release formulation (slow release) at higher administered doses. The present invention is directed to providing for an improved antibiotic product.

In accordance with one aspect of the present invention, there is provided an antibiotic pharmaceutical product which is comprised of at least two, preferably at least three, antibiotic dosage forms. Such dosage forms are formulated so that each of the dosage forms has a different release profile.

In a particularly preferred embodiment, there are at least two, preferably at least three dosage forms, each of which has a different release profile and the release profile of each of the dosage forms is such that the dosage forms each start release of the antibiotic contained therein at different times after administration of the antibiotic product.

Thus, in accordance with an aspect of the present invention, there is provided a single or unitary antibiotic product that has contained therein at least two, preferably at least three antibiotic dosage forms, each of which has a different release profile, whereby the antibiotic contained in each of such dosage forms is released at different times.

In accordance with a further aspect of the invention, the antibiotic product may be comprised of at least four different dosage forms, each of which starts to release the antibiotic contained therein at different times after administration of the antibiotic product.

The antibiotic product generally does not include more than five dosage forms with different release times.

In accordance with a preferred embodiment, the antibiotic product has an overall release profile such that when administered the maximum serum concentration of the total antibiotic released from the product is reached in less than twelve hours, preferably in less than eleven hours. In an embodiment, the maximum serum concentration of the total antibiotic released from the antibiotic product is achieved no earlier than four hours after administration.

In accordance with one preferred embodiment of the invention, there are at least three dosage forms. One of the at least three dosage forms is an immediate release dosage form whereby initiation of release of the antibiotic therefrom is not substantially delayed after administration of the antibiotic product. The second and third of the at least three dosage forms is a delayed dosage form (which may be a pH sensitive or a non-pH sensitive delayed dosage form, depending on the type of antibiotic product), whereby the antibiotic released therefrom is delayed until after initiation of release of the antibiotic from the immediate release dosage form. More particularly, the antibiotic release from the second of the at least two dosage forms achieves a $C_{max}$ (maximum serum concentration in the serum) at a time after the antibiotic released from the first of the at least three dosage forms achieves a $C_{max}$ in the serum, and the antibiotic released from the third dosage form achieves a $C_{max}$ in the serum after the $C_{max}$ of antibiotic released from the second dosage form.

In one embodiment, the second of the at least two dosage forms initiates release of the antibiotic contained therein at least one hour after the first dosage form, with the initiation of the release therefrom generally occurring no more than six hours after initiation of release of antibiotic from the first dosage form of the at least three dosage forms.

In general, the immediate release dosage form produces a $C_{max}$ for the antibiotic released therefrom within from about 0.5 to about 2 hours, with the second dosage form of the at least three dosage forms producing a $C_{max}$ for the antibiotic released therefrom in no more than about four hours. In general, the $C_{max}$ for such second dosage form is achieved no earlier than two hours after administration of the antibiotic product; however, it is possible within the scope of the invention to achieve $C_{max}$ in a shorter period of time.

As hereinabove indicated, the antibiotic product may contain at least three or at least four or more different dosage forms. For example, if the antibiotic product includes a third dosage form, the antibiotic released therefrom reaches a $C_{max}$ at a time later than the $C_{max}$ is achieved for the antibiotic released from each of the first and second dosage forms. In a preferred embodiment, release of antibiotic from the third dosage form is started after initiation of release of antibiotic from both the first dosage form and the second dosage form. In one embodiment, $C_{max}$ for antibiotic release from the third dosage form is achieved within eight hours.

In another embodiment, the antibiotic product contains at least four dosage foams, with each of the at least four dosage forms having different release profiles, whereby the antibiotic release from each of the at least four different dosage forms achieves a $C_{max}$ at a different time.

As hereinabove indicated, in a preferred embodiment, irrespective of whether the antibiotic contains at least two or at least three or at least four different dosage forms each with a different release profile, $C_{max}$ for all the antibiotic released from the antibiotic product is achieved in less than twelve hours, and more generally is achieved in less than eleven hours.

In a preferred embodiment, the antibiotic product is a once a day product, whereby after administration of the antibiotic product, no further product is administered during the day; i.e., the preferred regimen is that the product is administered only once over a twenty-four hour period. Thus, in accordance with the present invention, there is a single administration of an antibiotic product with the antibiotic being released in a manner such that overall antibiotic release is effected with different release profiles in a manner such that the overall $C_{max}$ for the antibiotic product is reached in less than twelve hours. The term single administration means that the total antibiotic administered over a twenty-four hour period is administered at the same time, which can be a single tablet or capsule or two or more thereof, provided that they are administered at essentially the same time.

Applicant has found that a single dosage antibiotic product comprised of at least three antibiotic dosage forms each having a different release profile is an improvement over a single dosage antibiotic product comprised of an antibiotic dosage form having a single release profile. Each of the dosage forms of antibiotic in a pharmaceutically acceptable carrier may have one or more antibiotics and each of the dosage forms may have the same antibiotic or different antibiotics.

It is to be understood that when it is disclosed herein that a dosage form initiates release after another dosage form, such terminology means that the dosage form is designed and is intended to produce such later initiated release. It is known in the art, however, notwithstanding such design and intent, some "leakage" of antibiotic may occur. Such "leakage" is not "release" as used herein.

If at least four dosage forms are used, the fourth of the at least four dosage form may be a sustained release dosage form or a delayed release dosage form. If the fourth dosage form is a sustained release dosage form, even though $C_{max}$ of the fourth dosage form of the at least four dosage forms is reached after the $C_{max}$ of each of the other dosage forms is reached, antibiotic release from such fourth dosage form may be initiated prior to or after release from the second or third dosage form.

The antibiotic product of the present invention, as hereinabove described, may be formulated for administration by a variety of routes of administration. For example, the antibiotic product may be formulated in a way that is suitable for topical administration; administration in the eye or the ear; rectal or vaginal administration; as nose drops; by inhalation; as an injectable; or for oral administration. In a preferred embodiment, the antibiotic product is formulated in a manner such that it is suitable for oral administration.

For example, in formulating the antibiotic product for topical administration, such as by application to the skin, the at least two different dosage forms, each of which contains an antibiotic, may be formulated for topical administration by including such dosage forms in an oil-in-water emulsion, or a water-in-oil emulsion. In such a formulation, the immediate release dosage form is in the continuous phase, and the delayed release dosage form is in a discontinuous phase. The formulation may also be produced in a manner for delivery of three dosage forms as hereinabove described. For example, there may be provided an oil-in-water-in-oil emulsion, with oil being a continuous phase that contains the immediate release component, water dispersed in the oil containing a first delayed release dosage form, and oil dispersed in the water containing a third delayed release dosage form.

It is also within the scope of the invention to provide an antibiotic product in the form of a patch, which includes antibiotic dosage forms having different release profiles, as hereinabove described.

In addition, the antibiotic product may be formulated for use in the eye or ear or nose, for example, as a liquid emulsion. For example, the dosage form may be coated with a hydrophobic polymer whereby a dosage form is in the oil phase of the emulsion, and a dosage form may be coated with hydrophilic polymer, whereby a dosage form is in the water phase of the emulsion.

Furthermore, the antibiotic product with at least three different dosage forms with different release profiles may be formulated for rectal or vaginal administration, as known in the art. This may take the form of a cream or emulsion, or other dissolvable dosage form similar to those used for topical administration.

As a further embodiment, the antibiotic product may be formulated for use in inhalation therapy by coating the particles and micronizing the particles for inhalation.

In a preferred embodiment, the antibiotic product is formulated in a manner suitable for oral administration. Thus, for example, for oral administration, each of the dosage forms may be used as a pellet or a particle, with a pellet or particle then being formed into a unitary pharmaceutical product, for example, in a capsule, or embedded in a tablet, or suspended in a liquid for oral administration.

Alternatively, in formulating an oral delivery system, each of the dosage forms of the product may be formulated as a tablet, with each of the tablets being put into a capsule to produce a unitary antibiotic product. Thus, for example, antibiotic products may include a first dosage form in the form of a tablet that is an immediate release tablet, and may also include two or more additional tablets, each of which provides for a delayed release of the antibiotic, as hereinabove described, whereby the $C_{max}$ of the antibiotic released from each of the tablets is reached at different times, with the $C_{max}$ of the total antibiotic released from the antibiotic product being achieved in less than twelve hours.

The formulation of an antibiotic product including at least three dosage forms with different release profiles for different routes of administration is deemed to be within the skill of the art from the teachings herein. As known in the art, with respect to delayed release, the time of release can be controlled by the concentration of antibiotics in the coating and/or the thickness of the coating.

In formulating an antibiotic product in accordance with the invention, in one embodiment, the immediate release dosage form of the product generally provides from about 20% to about 50% of the total dosage of antibiotic to be delivered by the product, with such immediate release dosage forms generally providing at least 25% of the total dosage of the antibiotic to be delivered by the product. In many cases, the immediate release dosage form provides from about 20% to about 30% of the total dosage of antibiotic to be delivered by the product; however, in some cases it may be desirable to have the immediate release dosage form provide for about 45% to about 50% of the total dosage of antibiotic to be delivered by the product.

The remaining dosage forms deliver the remainder of the antibiotic. If more than one delayed release dosage form is used, in one embodiment, each of the delayed release dosage forms may provide about equal amounts of antibiotic; however, they may also be formulated so as to provide different amounts.

In accordance with the present invention, each of the dosage forms contains the same antibiotic; however, each of the dosage forms may contain more than one antibiotic.

In one embodiment, where the composition contains one immediate release component and two delayed release components, the immediate release component provides from 20% to 35% (preferably 20% to 30%), by weight, of the total antibiotic; where there is three delayed release components, the immediate release component provides from 15% to 30%, by weight, of the total antibiotic; and where there are four delayed release components, the immediate release component provides from 10% to 25%, by weight, of the total antibiotic.

With respect to the delayed release components, where there are two delayed release components, the first delayed release component (the one released earlier in time) provides from 30% to 60%, by weight, of the total antibiotic provided by the two delayed release components with the second delayed release component providing the remainder of the antibiotic.

Where there are three delayed release components, the earliest released component provides 20% to 35% by weight of the total antibiotic provided by the three delayed release components, the next in time delayed release component provides from 20% to 40%, by weight, of the antibiotic provided by the three delayed release components and the last in time providing the remainder of the antibiotic provided by the three delayed release components.

When there are four delayed release components, the earliest delayed release component provides from 15% to 30%, by weight, the next in time delayed release component provides from 15% to 30%, the next in time delayed release component provides from 20% to 35%, by weight, and the last in time delayed release component provides from 20% to 35%, by weight, in each case of the total antibiotic provided by the four delayed release components.

The Immediate Release Component

The immediate release portion of this system can be a mixture of ingredients that breaks down quickly after administration to release the antibiotic. This can take the form of either a discrete pellet or granule that is mixed in with, or compressed with, the other three components.

The materials to be added to the antibiotics for the immediate release component can be, but are not limited to, microcrystalline cellulose, corn starch, pregelatinized starch, potato starch, rice starch, sodium carboxymethyl starch, hydroxypropylcellulose, hydroxypropylmethylcellulose, hydroxyethylcellulose, ethylcellulose, chitosan, hydroxychitosan, hydroxymethylatedchitosan, cross-linked chitosan, cross-linked hydroxymethyl chitosan, maltodextrin, mannitol, sorbitol, dextrose, maltose, fructose, glucose, levulose, sucrose, polyvinylpyrrolidone (PVP), acrylic acid derivatives (Carbopol, Eudragit, etc.), polyethylene glycols, such a low molecular weight PEGs (PEG2000-10000) and high molecular weight PEGs (Polyox) with molecular weights above 20,000 daltons.

It may be useful to have these materials present in the range of 1.0 to 60% (W/W).

In addition, it may be useful to have other ingredients in this system to aid in the dissolution of the drug, or the breakdown of the component after ingestion or administration. These ingredients can be surfactants, such as sodium lauryl sulfate, sodium monoglycerate, sorbitan monooleate, sorbitan monooleate, polyoxyethylene sorbitan monooleate, glyceryl monostearate, glyceryl monooleate, glyceryl monobutyrate, one of the non-ionic surfactants such as the Pluronic line of surfactants, or any other material with surface active properties, or any combination of the above.

These materials may be present in the rate of 0.05-15% (W/W).

The Non-pH Sensitive Delayed Release Component

The components in this composition are the same immediate release unit, but with additional polymers integrated into the composition, or as coatings over the pellet or granule.

Materials that can be used to obtain a delay in release suitable for this component of the invention can be, but are not limited to, polyethylene glycol (PEG) with molecular weight above 4,000 daltons (Carbowax, Polyox), waxes such as white wax or bees wax, paraffin, acrylic acid derivatives (Eudragit), propylene glycol, and ethylcellulose.

Typically these materials can be present in the range of 0.5-25% (W/W) of this component.

The pH Sensitive (Enteric) Release Component

The components in this composition are the same as the immediate release component, but with additional polymers integrated into the composition, or as coatings over the pellet or granule.

The kind of materials useful for this purpose can be, but are not limited to, cellulose acetate pthalate, Eudragit L, and other pthalate salts of cellulose derivatives.

These materials can be present in concentrations from 4-20% (W/W).

Sustained Release Component

The components in this composition are the same as the immediate release component, but with additional polymers integrated into the composition, or as coatings over the pellet or granule.

The kind of materials useful for this purpose can be, but are not limited to, ethylcellulose, hydroxypropylmethylcellulose, hydroxypropyl cellulose, hydroxyethylcellulose, carboxymethylcellulose, methylcellulose, nitrocellulose, Eudragit R, and Eudragit RL, Carbopol, or polyethylene glycols with molecular weights in excess of 8,000 daltons.

These materials can be present in concentrations from 4-20% (W/W).

As hereinabove indicated, the units comprising the antibiotic composition of the present invention can be in the form of discrete pellets or particles contained in the capsule, or particles embedded in a tablet or suspended in a liquid suspension.

The antibiotic composition of the present invention may be administered, for example, by any of the following routes of administration: sublingual, transmucosal, transdermal, parenteral, etc., and preferably is administered orally. The composition includes a therapeutically effective amount of the antibiotic, which amount will vary with the antibiotic to be used, the disease or infection to be treated, and the number of times that the composition is to be delivered in a day. The composition is administered to a host in an amount effective for treating a bacterial infection.

This system will be especially useful in extending the practical therapeutic activity for antibiotics with elimination half lives of less than 20 hours and more particularly with elimination half-lives of less than 12 hours, and will be particularly useful for those drugs with half-lives of 2-10 hours. The following are examples of some antibiotics with half-lives of about 1 to 12 hours: Cefadroxil, cefazolin, cephalexin, cephalothin, cephapirin, cephacelor, cephprozil, cephadrine, cefamandole, cefonicid, ceforanide, cefuroxime, cefixime, cefoperazone, cefotaxime, cefpodoxime, ceftaxidime, ceftibuten, ceftizoxime, ceftriaxone, cefepime, cefmetazole, cefotetan, cefoxitin, loracarbef, imipenem, erythromycin (and erythromycin salts such as estolate, ethylsuccinate, gluceptate, lactobionate, stearate), azithromycin, clarithromycoin, dirithromycin, troleanomycin, penicillin V, peniciliin salts, and complexes, methicillin, nafcillin, oxacillin, cloxacillin, dicloxacillin, amoxicillin, amoxicillin and clavulanate potassium, ampicillin, bacampicillin, carbenicillin indanyl sodium (and other salts of carbenicillin) piperacillin, piperacillin and taxobactam, ticarcillin, ticarcillin and clavulanate potassium, clindamycin, vancomycin, novobiocin, aminosalicylic acid, capreomycin, cycloserine, ethambutol HCl and other salts, ethionamide, and isoniazid, ciprofloxacin, levofloxacin, lomefloxacin, nalidixic acid, norfloxacin, ofloxacin, sparfloxacin, sulfacytine, suflamerazine, sulfamethazine, sulfamethixole, sulfasalazine, sulfisoxazole, sulfapyrizine, sulfadiazine, sulfmethoxazole, sulfapyridine, metronidazole, methenamine, fosfomycin, nitrofurantoin, trimethoprim, clofazimine, co-triamoxazole, pentamidine, and trimetrexate.

The invention will be further described with respect to the following examples; however, the scope of the invention is not limited thereby. All percentages in this specification, unless otherwise specified, are by weight.

EXAMPLES

Immediate Release Component

Formulate the composition by mixing the ingredients in a suitable pharmaceutical mixer or granulator such as a planetary mixer, high-shear granulator, fluid bed granulator, or extruder, in the presence of water or other solvent, or in a dry blend. If water or other solvent was used, dry the blend in a suitable pharmaceutical drier, such as a vacuum over or forced-air oven. The product may be sieved or granulated, and compressed using a suitable tablet press, such as a rotary tablet press.

| | Ingredient | Conc. (% W/W) |
|---|---|---|
| Example 1: | Amoxicillin | 65% (W/W) |
| | Microcrystalline cellulose | 20 |
| | Povidone | 10 |
| | Croscarmellose sodium | 5 |
| Example 2: | Amoxicillin | 55% (W/W) |
| | Microcrystalline cellulose | 25 |
| | Povidone | 10 |
| | Croscarmellose sodium | 10 |
| Example 3: | Amoxicillin | 65% (W/W) |
| | Microcrystalline cellulose | 20 |
| | Hydroxypropylcellulose | 10 |
| | Croscarmellose sodium | 5 |
| Example 4: | Amoxicillin | 75% (W/W) |
| | Polyethylene glycol 4000 | 10 |
| | Polyethylene glycol 2000 | 10 |
| | Hydroxypropylcellulose | 5 |
| Example 5: | Amoxicillin | 75% (W/W) |
| | Polyethylene glycol 8000 | 20 |
| | Polyvinylpyrrolidone | 5 |
| Example 6: | Clarithromycin | 65% (W/W) |
| | Microcrystalline cellulose | 20 |
| | Hydroxypropylcellulose | 10 |
| | Croscarmellose sodium | 5 |
| Example 7: | Clarithromycin | 75% (W/W) |
| | Microcrystalline cellulose | 15 |
| | Hydroxypropylcellulose | 5 |
| | Croscarmellose sodium | 5 |
| Example 8: | Clarithromycin | 75% (W/W) |
| | Polyethylene glycol 4000 | 10 |
| | Polyethylene glycol 2000 | 10 |
| | Hydroxypropylcellulose | 5 |
| Example 9: | Clarithromycin | 75% (W/W) |
| | Polyethylene glycol 8000 | 20 |
| | Polyvinylpyrrolidone | 5 |
| Example 10: | Ciprofloxacin | 65% (W/W) |
| | Microcrystalline cellulose | 20 |
| | Hydroxypropylcellulose | 10 |
| | Croscarmellose sodium | 5 |
| Example 11: | Ciprofloxacin | 75% (W/W) |
| | Microcrystalline cellulose | 15 |
| | Hydroxypropylcellulose | 5 |
| | Croscarmellose sodium | 5 |
| Example 12: | Ciprofloxacin | 75% (W/W) |
| | Polyethylene glycol 4000 | 10 |
| | Polytheylene glycol 2000 | 10 |
| | Hydroxypropylcellulose | 5 |
| Example 13: | Cirpofloxacin | 75% (W/W) |
| | Polyethylene glycol 8000 | 20 |
| | Polyvinylpyrrolidone | 5 |
| Example 14: | Ceftibuten | 75% (W/W) |
| | Polyethylene glycol 4000 | 10 |
| | Polyethylene glycol 2000 | 10 |
| | Hydroxypropylcellulose | 5 |
| Example 15: | Ceftibuten | 75% (W/W) |
| | Polyethylene Glycol 4000 | 20 |
| | Polyvinylpyrrolidone | 5 |

Non-pH Sensitive Delayed Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| | Ingredient | Conc. (% W/W) |
|---|---|---|
| Example 16: | Amoxicillin | 65% (W/W) |
| | Microcrystalline cellulose | 20 |
| | Polyox | 10 |
| | Croscarmellose sodium | 5 |
| Example 17: | Amoxicillin | 55% (W/W) |
| | Microcrystalline cellulose | 25 |
| | Polyox | 10 |
| | Glyceryl monooleate | 10 |
| Example 18: | Amoxicillin | 65% (W/W) |
| | Polyox | 20 |
| | Hydroxypropylcellulose | 10 |
| | Croscarmellose sodium | 5 |
| Example 19: | Clarithromycin | 70% (W/W) |
| | Polyox | 20 |
| | Hydroxypropylcellulose | 5 |
| | Croscarmellose sodium | 5 |

Enteric Release Component

Formulate the ingredients by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

| | Ingredient | Conc. (% W/W) |
|---|---|---|
| Example 20: | Amoxicillin | 65% (W/W) |
| | Microcrystalline cellulose | 20 |
| | Cellulose Acetate Pthalate | 15 |
| Example 21: | Amoxicillin | 55% (W/W) |
| | Microcrystalline cellulose | 25 |
| | Cellulose Acetate Pthalate | 10 |
| | Hydroxypropylmethylcellulose | 10 |
| Example 22: | Amoxicillin | 65% (W/W) |
| | Polyox | 20 |
| | Hydroxypropylcellulose pthalate | 10 |
| | Eudragit L30D | 5 |
| Example 23: | Amoxicillin | 40% (W/W) |
| | Microcrystalline Cellulose | 40 |
| | Cellulose Acetate Pthalate | 10 |
| Example 24: | Clarithromycin | 70% (W/W) |
| | Hydroxypropylcellulose pthalate | 15 |
| | Croscarmellose sodium | 10 |
| Example 25: | Clarithromycin | 75% (W/W) |
| | Polyethylene glycol 2000 | 10 |
| | Eudragit E 30D | 15 |
| Example 26: | Clarithromycin | 40% (W/W) |
| | Lactose | 50 |
| | Eudgragit L 30D | 10 |
| Example 27: | Ciprofloxacin | 65% (W/W) |
| | Microcrystalline Cellulose | 20 |
| | Eudragit L 30D | 10 |
| Example 28: | Ciprofloxacin | 75% (W/W) |
| | Microcrystalline Cellulose | 15 |
| | Hydroxypropylcellulose pthalate | 10 |
| Example 29: | Ciprofloxacin | 80% (W/W) |
| | Lactose | 10 |
| | Eudragit L 30D | 10 |
| Example 30: | Ciprofloxacin | 70% (W/W) |
| | Polyethylene glycol 4000 | 20 |
| | Cellulose acetate pthalate | 10 |
| Example 31: | Ceftibuten | 60% (W/W) |
| | Polyethylene glycol 2000 | 10 |
| | Lactose | 20 |
| | Eudragit L 30D | 10 |
| Example 32: | Ceftibuten | 70% (W/W) |
| | Microcrystalline cellulose | 20 |
| | Cellulose acetate pthalate | 10 |

Sustained Release Component

Formulate the composition by mixing the ingredients in a suitable pharmaceutical mixer or granulator such as a planetary mixer, high-shear granulator, fluid bed granulator, or extruder, in the presence of water or other solvent, or in a hot melt process. If water or other solvent was used, dry the blend in a suitable pharmaceutical drier, such as a vacuum over or forced-air oven. Allow the product to cool, the product may be sieved or granulated, and compressed using a suitable tablet press, such as a rotary tablet press.

|  | Ingredient | Conc. (% W/W) |
|---|---|---|
| Example 33: | Amoxicillin | 65% (W/W) |
|  | Ethylcellulose | 20 |
|  | Polyox | 10 |
|  | Hydroxypropylmethylcellulose | 5 |
| Example 34: | Amoxicillin | 55% (W/W) |
|  | Lactose | 25 |
|  | Polyox | 10 |
|  | Glyceryl monooleate | 10 |
| Example 35: | Amoxicillin | 70% (W/W) |
|  | Polyox | 20 |
|  | Hydroxypropylcellulose | 10 |
| Example 36: | Clarithromycin | 75% (W/W) |
|  | Lactose | 15 |
|  | Hydroxypropylcellulose | 5 |
|  | Ethylcellulose | 5 |
| Example 37: | Clarithromycin | 75% (W/W) |
|  | Polyethylene glycol 4000 | 10 |
|  | Lactose | 10 |
|  | Eudragit RL 30D | 5 |
| Example 38: | Clarithromycin | 80% (W/W) |
|  | Polyethylene glycol 8000 | 10 |
|  | Hydroxypropylmethylcellulose | 5 |
|  | Eudragit RS 30D | 5 |
| Example 39: | Ciprofloxacin | 75% (W/W) |
|  | Hydroxyethylcellulose | 10 |
|  | Polyethylene glycol 4000 | 10 |
|  | Hydroxypropylcellulose | 5 |
| Example 40: | Ciprofloxacin | 75% (W/W) |
|  | Lactose | 10 |
|  | Povidone (PVP) | 10 |
|  | Polyethylene glycol 2000 | 5 |
| Example 41: | Ceftibuten | 75% (W/W) |
|  | Polyethylene glycol 4000 | 10 |
|  | Povidone (PVP) | 10 |
|  | Hydroxypropylcellulose | 5 |
| Example 42: | Ceftibuten | 75% (W/W) |
|  | Lactose | 15 |
|  | Polyethylene glycol 4000 | 5 |
|  | Polyvinylpyrrolidone | 5 |

Three Pulses

Example 43

1. Metronidazole Matrix Pellet Formulation and Preparation Procedure (Immediate Release)
A. Pellet Formulation
The composition of the metronidazole matrix pellets provided in Table 1.

TABLE 1

Composition of Metronidazole Pellets

| Component | Percentage (%) |
|---|---|
| Metronidazole | 50 |
| Avicel PH 101 | 20 |

TABLE 1-continued

Composition of Metronidazole Pellets

| Component | Percentage (%) |
|---|---|
| Lactose | 20 |
| PVP K29/32* | 10 |
| Purified Water | |
| Total | 100 |

*PVP K29/32 was added as a 20% w/w aqueous solution during wet massing.

B. Preparation Procedure for Metronidazole Matrix Pellets
1.2.1 Blend metronidazole and Avicel® PH 101 using a Robot Coupe high shear granulator.
1.2.2 Add 20% Povidone K29/32 binder solution slowly into the powder blend under continuous mixing.
1.2.3 Extrude the wet mass using an LCI Bench Top Granulator. The diameter of the screen of the Bench Top Granulator was 1.0 mm.
1.2.4 Spheronize the extrudate using a Model SPH20 Caleva Spheronizer.
1.2.5 Dry the spheronized pellets at 50° C. overnight.
1.2.6 Pellets between 16 and 30 Mesh were collected for further processing.
1.3 Preparation of an Eudragit® L 30 D-55 Aqueous Coating Dispersion
A. Dispersion Formulation
The composition of the aqueous Eudragit L30D-55 dispersion applied to the metronidazole matrix pellets is provided below in Table 2.

TABLE 2

Eudragit ® L 30 D-55 Aqueous Coating Dispersion

| Component | Percentage (%) |
|---|---|
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

B. Preparation Procedure for an Eudragit® L 30 D-55 Aqueous Dispersion
1.3.1 Suspend triethyl citrate and talc in deionized water.
1.3.2 The TEC/talc suspension is then homogenized using a PowerGen 700 high shear mixer.
1.3.3 Add the TEC/talc suspension slowly to the Eudragit® L 30 D-55 latex dispersion while stirring.
1.3.4 Allow the coating dispersion to stir for one hour prior to application onto the metronidazole matrix pellets.
1.4 Preparation of an Eudragit® S 100 Aqueous Coating Dispersion
A. Dispersion Formulation
The composition of the aqueous Eudragit® S 100 dispersion applied to the metronidazole matrix pellets is provided below in Table 3.

TABLE 3

Eudragit ® S 100 Aqueous Coating Dispersion

| Component | Percentage (%) |
|---|---|
| Part A | |
| Eudragit ® S 100 | 12.0 |
| 1N Ammonium Hydroxide | 6.1 |

TABLE 3-continued

Eudragit® S 100 Aqueous Coating Dispersion

| Component | Percentage (%) |
|---|---|
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

B. Preparation Procedure for an Eudragit® S 100 Aqueous Dispersion

Part I:
(i) Dispense Eudragit® S 100 powder in deionized water with stirring.
(ii) Add ammonium hydroxide solution drop-wise into the dispersion with stirring.
(iii) Allow the partially neutralized dispersion to stir for 60 minutes.
(iv) Add triethyl citrate drop-wise into the dispersion with stirring. Stir for about 2 hours prior to the addition of Part B.

Part II:
(i) Disperse talc in the required amount of water
(ii) Homogenize the dispersion using a PowerGen 700D high shear mixer.
(iii) Part B is then added slowly to the polymer dispersion in Part A with a mild stirring.

1.5 Coating Conditions for the Application of Aqueous Coating Dispersions

The following coating parameters were used to coat matrix pellets with each of the Eudragit® L 30 D-55 and Eudragit® S 100 aqueous film coating.

| | |
|---|---|
| Coating Equipment | STREA 1™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

(i) Coat matrix pellets with L30 D-55 dispersion such that you apply 12% coat weight gain to the pellets.
(ii) Coat matrix pellets with S100 dispersion such that you apply 20% coat weight gain to the pellets.

1.6 Encapsulation of the Metronidazole Pellets

Pellets are filled into size 00 hard gelatin capsules at a ratio of 30%:30%:40%:
Immediate-release matrix pellets uncoated, L30 D-55 coated pellets and S100 coated pellets respectively.
The capsule is filled with the three different pellets to achieve a total dose of 375 mg/capsule.

Three Pulses

Example 44

Amoxicillin Pellet Formulation and Preparation Procedure 44.1 Pellet Formulations for Subsequent Coating
The composition of the Amoxicillin trihydrate matrix pellets provided in Table 4.

TABLE 4

Composition of Amoxicillin Matrix Pellets

| Component | Percentage (%) |
|---|---|
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

44.2 Preparation Procedure for Amoxicillin Matrix Pellets 44.2.1 Blend Amoxicillin and Avicel® PH 101 using a low shear blender.

44.2.2 Add the hydroxypropyl methylcellulose binder solution slowly into the powder blend under continuous mixing.

44.2.3 Extrude the wet mass using an LCI Bench. Top Granulator. The diameter of the screen of the Bench Top Granulator is 0.8 mm.

44.2.4 Spheronize the extrudate using a QJ-230 Spheronizer using a small cross section plate.

44.2.5 Dry the spheronized pellets at 60° C. using a fluid bed dryer until the exhaust temperature reaches 40° C.

44.2.6 Pellets between 20 and 40 Mesh were collected for further processing.

44.3 Preparation of an Eudragit® L 30 D-55 Aqueous Coating Dispersion 44.3.1 Dispersion Formulation The composition of the aqueous Eudragit L30D-55 dispersion applied to the amoxicillin matrix pellets is provided below in Table 5.

TABLE 5

Eudragit® L 30 D-55 Aqueous Coating Dispersion

| Component | Percentage (%) |
|---|---|
| Eudragit® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

44.4 Preparation Procedure for an Eudragit® L 30 D-55 Aqueous Dispersion 44.4.1 Suspend triethyl citrate and talc in deionized water.

44.4.2 The TEC/talc suspension is mixed using laboratory mixer.

44.4.3 Add the TEC/talc suspension from slowly to the Eudragit® L 30 D-55 latex dispersion while stirring.

44.4.4 Allow the coating dispersion to stir for one hour prior to application onto the amoxicillin matrix pellets.

44.5 Preparation of an Eudragit® S 100 Aqueous Coating Dispersion 44.5.1 Dispersion Formulation The composition of the aqueous Eudragit® S 100 dispersion applied to the Amoxicillin matrix pellets is provided below in Table 6.

TABLE 6

Eudragit® S 100 Aqueous Coating Dispersion

| Component | Percentage (%) |
|---|---|
| Part A | |
| Eudragit® S 100 | 10.0 |
| 1N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

44.6 Preparation Procedure for an Eudragit® S 100 Aqueous Dispersion

Part A:

44.6.1 Dispense Eudragit® S 100 powder in deionized water with stirring.

44.6.2 Add ammonium hydroxide solution drop-wise into the dispersion with stirring.

44.6.3 Allow the partially neutralized dispersion to stir for 60 minutes.

44.6.4 Add triethyl citrate drop-wise into the dispersion with stirring and let stir overnight prior to the addition of Part B.

Part B:

44.6.5 Disperse talc in the required amount of water 44.6.6 Stir the dispersion using an overhead laboratory mixer.

44.6.7 Part B is then added slowly to the polymer dispersion in Part A with a mild stirring.

44.7 Coating Conditions for the Application of Aqueous Coating Dispersions

The following coating parameters were used for both the Eudragit® L 30 D-55 and Eudragit® S 100 aqueous film coating processes.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2-6 gram per minute |

44.7.1 Coat matrix pellets with L30 D-55 dispersion such that you apply 20% coat weight gain to the pellets.

44.7.2 Coat matrix pellets with S100 dispersion such that you apply 37% coat weight gain to the pellets.

44.8 Preparation of Amoxicillin Granulation (Immediate Release Component) for Tabletting

TABLE 7

Composition of Amoxicillin Granulation

| Component | Percentage (%) |
|---|---|
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

44.8.1 Blend Amoxicillin and Avicel® PH 101 using a low shear blender.

44.8.2 Add the hydroxypropyl methylcellulose binder solution slowly into the powder blend under continuous mixing.

44.8.3 Dry the granulation at 60° C. using a fluid bed dryer until the exhaust temperature reaches 40° C.

44.8.4 Granules between 20 and 40 Mesh are collected for further processing.

44.9 Tabletting of the Amoxicillin Pellets

TABLE 8

Composition of Amoxicillin Tablets

| Component | Percentage (%) |
|---|---|
| Amoxicillin granules | 32.5 |
| Avicel PH 200 | 5.0 |
| Amoxicillin L30D-55 coated pellets | 30 |
| Amoxicillin S100 coated pellets | 30 |
| Colloidal silicon dioxide | 1.5 |
| Magnesium stearate | 1.0 |
| Total | 100 |

44.9.1 Blend the Amoxicillin granules, Avicel PH-200, Amoxicillin pellets and colloidal silicon dioxide for 15 minutes in a tumble blender.

44.9.2 Add the magnesium stearate to the blender, and blend for 5 minutes.

44.9.3 Compress the blend on a rotary tablet press.

44.9.4 The fill weight should be adjusted to achieve a 500 mg dose tablet.

Three Pulses

Example 45

Clarithromycin Pellet Formulation and Preparation Procedure 45.1 Pellet Formulation The composition of the clarithromycin matrix pellets provided in Table 1.

TABLE 9

Composition of Clarithromycin Pellets

| Component | Percentage (%) |
|---|---|
| Clarithromycin | 50.6 |
| Lactose monohydrate, spray dried | 32.1 |
| Silicified microcrystalline cellulose | 14.6 |
| Polyoxyl 35 Castor Oil* | 1.7 |
| Hydroxypropyl methylcellulose* | 1.0 |
| Total | 100 |

*Hydroxypropyl methylcellulose and Polyoxyl 35 were added as an 8.7% w/w aqueous solution during wet massing.

45.2 Preparation Procedure for Clarithromycin Matrix Pellets 45.2.1 Blend clarithromycin, silicified microcrystalline cellulose and lactose monohydrate using a Robot Coupe high shear granulator.

45.2.2 Prepare the binder solution by adding the Polyoxyl to the purified water while stirring. After that is mixed, slowly add the hydroxypropyl methylcellulose and continue to stir until a solution is achieved.

45.2.3 Add binder solution slowly into the powder blend under continuous mixing.

45.2.4 Granulate the powders in the high shear granulator with the binder solution.

45.2.5 Extrude the wet mass using an LCI Bench Top Granulator. The diameter of the screen of the Bench Top Granulator was 1.2 mm.

45.2.6 Spheronize the extrudate using a Model SPH20 Caleva Spheronizer.

45.2.7 Dry the spheronized pellets at 50° C. overnight.

45.2.8 Pellets between 18 and 30 Mesh were collected for further processing.

45.3 Preparation of an Eudragit® L 30 D-55 Aqueous Coating Dispersion 45.3.1 Dispersion Formulation The composition of the aqueous Eudragit L30D-55 dispersion applied to the clarithromycin matrix pellets is provided below in Table 10.

TABLE 10

Eudragit ® L 30 D-55 Aqueous Coating Dispersion

| Component | Percentage (%) |
|---|---|
| Eudragit ® L 30 D-55 | 40.4 |
| Triethyl Citrate | 1.8 |
| Talc | 6.1 |
| Water | 51.7 |
| Solids Content | 20.0 |
| Polymer Content | 12.1 |

45.4 Preparation Procedure for an Eudragit® L 30 D-55 Aqueous Dispersion 45.4.1 Suspend triethyl citrate and talc in deionized water.

45.4.2 The TEC/talc suspension is then homogenized using a PowerGen 700 high shear mixer.

45.4.3 Add the suspension from 4.2.2 slowly to the Eudragit® L 30 D-55 latex dispersion while stirring.

45.4.4 Allow the coating dispersion to stir for one hour prior to application onto the clarithromycin matrix pellets.

45.5 Preparation of an Eudragit® S 100 Aqueous Coating Dispersion 45.5.1 Dispersion Formulation The composition of the aqueous Eudragit® S 100 dispersion applied to the clarithromycin matrix pellets is provided below in Table 11.

TABLE 11

Eudragit ® S 100 Aqueous Coating Dispersion

| Component | Percentage (%) |
|---|---|
| Part A | |
| Eudragit ® S 100 | 10.0 |
| 1N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

45.6 Preparation Procedure for an Eudragit® S 100 Aqueous Dispersion

Part A:

45.6.1 Dispense Eudragit® S 100 powder in deionized water with stirring.

45.6.2 Add ammonium hydroxide solution drop-wise into the dispersion with stirring.

45.6.3 Allow the partially neutralized dispersion to stir for 60 minutes 45.6.4 Add the triethyl citrate drop-wise to the dispersion and stir for 60 minutes prior to the addition of Part B.

Part B:

45.6.5 Disperse talc in the required amount of water 45.6.6 Homogenize the dispersion using a PowerGen 700D high shear mixer.

45.6.7 Part B is then added slowly to the polymer dispersion in Part A with a mild stirring.

45.7 Coating Conditions for the Application of Aqueous Coating Dispersions

The following coating parameters were used for coating the matrix pellets with each of the Eudragit® L 30 D-55 and Eudragit® S 100 aqueous film coating.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.6 Bar |
| Pump Rate | 2 gram per minute |

45.7.1 Coat matrix pellets with L30 D-55 dispersion such that you apply 20% coat weight gain to the pellets.

45.7.2 Coat matrix pellets with S100 dispersion such that you apply 37% coat weight gain to the pellets.

4. Capsules were filled with the uncoated pellets, the L30D-55 coated pellets and S100 coated pellets in weight percentages of 30%:30%:40%, respectively to provide 250 mg. capsules.

Four Pulses

Example 46

1 Metronidazole Matrix Pellet Formulation and Preparation Procedure 46.1 Pellet Formulation The composition of the metronidazole matrix pellets provided in Table 12.

TABLE 12

Composition of Metronidazole Pellets

| Component | Percentage (%) |
|---|---|
| Metronidazole | 50 |
| Avicel PH 101 | 20 |
| Lactose | 20 |
| PVP K29/32* | 10 |
| Purified Water | |
| Total | 100 |

*PVP K29/32 was added as a 20% w/w aqueous solution during wet massing.

46.2 Preparation Procedure for Metronidazole Matrix Pellets
- 46.2.1 Blend metronidazole and Avicel® PH 101 using a Robot Coupe high shear granulator.
- 46.2.2 Add 20% Povidone K29/32 binder solution slowly into the powder blend under continuous mixing.
- 46.2.3 Extrude the wet mass using an LCI Bench Top Granulator. The diameter of the screen of the Bench Top Granulator was 1.0 mm.
- 46.2.4 Spheronize the extrudate using a Model SPH20 Caleva Spheronizer.
- 46.2.5 Dry the spheronized pellets at 50° C. overnight.
- 46.2.6 Pellets between 16 and 30 Mesh were collected for further processing.

46.3 Preparation of an Eudragit® L 30 D-55 Aqueous Coating Dispersion 46.3.1 Dispersion Formulation The composition of the aqueous Eudragit L30D-55 dispersion applied to the metronidazole matrix pellets is provided below in Table 13.

TABLE 13

Eudragit ® L 30 D-55 Aqueous Coating Dispersion

| Component | Percentage (%) |
| --- | --- |
| Eudragit ® L 30 D-55 | 55.0 |
| Triethyl Citrate | 1.6 |
| Talc | 8.0 |
| Purified Water | 37.4 |
| Solids Content | 25.5 |
| Polymer Content | 15.9 |

46.4 Preparation Procedure for an Eudragit® L 30 D-55 Aqueous Dispersion
- 46.4.1 Suspend triethyl citrate and talc in deionized water.
- 46.4.2 The TEC/talc suspension is then homogenized using a PowerGen 700 high shear mixer.
- 46.4.3 Add the TEC/talc suspension slowly to the Eudragit® L 30 D-55 latex dispersion while stirring.
- 46.4.4 Allow the coating dispersion to stir for one hour prior to application onto the metronidazole matrix pellets.

46.5 Preparation of an Eudragit® S 100 Aqueous Coating Dispersion 46.5.1 Dispersion Formulation The composition of the aqueous Eudragit® S 100 dispersion applied to the metronidazole matrix pellets is provided below in Table 14.

TABLE 14

Eudragit ® S 100 Aqueous Coating Dispersion

| Component | Percentage (%) |
| --- | --- |
| Part A | |
| Eudragit ® S 100 | 12.0 |
| 1N Ammonium Hydroxide | 6.1 |
| Triethyl Citrate | 6.0 |
| Purified Water | 65.9 |
| Part B | |
| Talc | 2.0 |
| Purified Water | 8.0 |
| Solid Content | 20.0 |
| Polymer Content | 12.0 |

46.6 Preparation Procedure for an Eudragit® S 100 Aqueous Dispersion

Part A:
- 46.6.1 Dispense Eudragit® S 100 powder in deionized water with stirring.
- 46.6.2 Add ammonium hydroxide solution drop-wise into the dispersion with stirring.
- 46.6.3 Allow the partially neutralized dispersion to stir for 60 minutes.
- 46.6.4 Add triethyl citrate drop-wise into the dispersion with stirring. Stir for about 2 hours prior to the addition of Part B.

Part B:
- 46.6.5 Disperse talc in the required amount of water
- 46.6.6 Homogenize the dispersion using a PowerGen 700D high shear mixer.
- 46.6.7 Part B is then added slowly to the polymer dispersion in Part A with a mild stirring.

46.7 Coating Conditions for the Application of Aqueous Coating Dispersions

The following coating parameters were used for coating with each of the Eudragit® L 30 D-55 and Eudragit® S 100 aqueous film coatings.

| Coating Equipment | STREA 1 ™ Table Top Laboratory Fluid Bed Coater |
| --- | --- |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2 gram per minute |

- 46.7.1 Coat matrix pellets with L30 D-55 dispersion such that you apply 12% coat weight gain to the pellets.
- 46.7.2 Coat matrix pellets with L30 D-55 dispersion such that you apply 30% coat weight gain to the pellets.
- 46.7.3 Coat matrix pellets with S100 dispersion such that you apply 20% coat weight gain to the pellets.

46.8 Encapsulation of the Metronidazole Pellets

Pellets are filled into size 00 hard gelatin capsules at a ratio of 20%:30%:20%:30% Immediate-release matrix pellets (uncoated), L30 D-55 coated pellets 12% weight, gain, L30D-55 coated pellets 30% weight gain and S100 coated pellets respectively. The capsule is filled with the four different pellets to achieve a total dose of 375 mg/capsule.

Four Pulses

Example 47

Amoxicillin Pellet Formulation and Preparation Procedure 47.1 Pellet Formulations The composition of the Amoxicillin trihydrate matrix pellets provided in Table 15.

TABLE 15

Composition of Amoxicillin Matrix Pellets

| Component | Percentage (%) |
| --- | --- |
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.2 Preparation Procedure for Amoxicillin Matrix Pellets 47.2.1 Blend Amoxicillin and Avicel® PH 101 using a low shear blender.

47.2.2 Add the hydroxypropyl methylcellulose binder solution slowly into the powder blend under continuous mixing.

47.2.3 Extrude the wet mass using an LCI Bench Top Granulator. The diameter of the screen of the Bench Top Granulator is 0.8 mm.

47.2.4 Spheronize the extrudate using a QJ-230 Spheronizer using a small cross section plate.

47.2.5 Dry the spheronized pellets at 60° C. using a fluid bed dryer until the exhaust temperature reaches 40° C.

47.2.6 Pellets between 20 and 40 Mesh were collected for further processing.

47.3 Preparation of an Eudragit® L 30 D-55 Aqueous Coating Dispersion 47.3.1 Dispersion Formulation The composition of the aqueous Eudragit L30D-55 dispersion applied to the amoxicillin matrix pellets is provided below in Table 16.

TABLE 16

| Eudragit ® L 30 D-55 Aqueous Coating Dispersion | |
| --- | --- |
| Component | Percentage (%) |
| Eudragit ® L 30 D-55 | 41.6 |
| Triethyl Citrate | 2.5 |
| Talc | 5.0 |
| Purified Water | 50.9 |
| Solids Content | 20.0 |
| Polymer Content | 12.5 |

47.4 Preparation Procedure for an Eudragit® L 30 D-55 Aqueous Dispersion 47.4.1 Suspend triethyl citrate and talc in deionized water.

47.4.2 The TEC/talc suspension is mixed using laboratory mixer.

47.4.3 Add the TEC/talc suspension from slowly to the Eudragit® L 30 D-55 latex dispersion while stirring.

47.4.4 Allow the coating dispersion to stir for one hour prior to application onto the amoxicillin matrix pellets.

47.5 Preparation of an Eudragit® S 100 Aqueous Coating Dispersion 47.6 Dispersion Formulation The composition of the aqueous Eudragit® S 100 dispersion applied to the Amoxicillin matrix pellets is provided below in Table 17.

TABLE 17

| Eudragit ® S 100 Aqueous Coating Dispersion | |
| --- | --- |
| Component | Percentage (%) |
| Part A | |
| Eudragit ® S 100 | 10.0 |
| 1N Ammonium Hydroxide | 5.1 |
| Triethyl Citrate | 5.0 |
| Water | 64.9 |
| Part B | |
| Talc | 2.0 |
| Water | 10.0 |
| Solid Content | 25.0 |
| Polymer Content | 10.0 |

47.7 Preparation Procedure for an Eudragit® S 100 Aqueous Dispersion

Part A:

47.7.1 Dispense Eudragit® S 100 powder in deionized water with stirring.

47.7.2 Add ammonium hydroxide solution drop-wise into the dispersion with stirring.

47.7.3 Allow the partially neutralized dispersion to stir for 60 minutes.

47.7.4 Add triethyl citrate drop-wise into the dispersion with stirring and let stir overnight prior to the addition of Part B.

Part B:

47.7.5 Disperse talc in the required amount of water 47.7.6 Stir the dispersion using an overhead laboratory mixer.

47.7.7 Part B is then added slowly to the polymer dispersion in Part A with a mild stirring.

47.8 Preparation of Aquacoat Coating Dispersion 47.8.1 Dispersion Formulation

The composition of the aqueous Aquacoat dispersion applied to Amoxicillin L30 D-55 coated pellets is provided below in Table 18.

TABLE 18

| Component | Percentage (%) |
| --- | --- |
| Aquacoat ECD | 79.3 |
| Hydroxypropyl methylcellulose | 15.9 |
| Dibutyl Sebacate | 4.8 |
| Purified Water (300 g) | |

47.8.1.1 Prepare Hydroxypropyl methylcellulose (Methocel E15) solution by dispersing in water with continuous stirring.

47.8.1.2 Add Aquacoat and dibutyl sebacate to the dispersion with stirring and continue to stir overnight.

47.9 Coating Conditions for the Application of Aqueous Coating Dispersions

The following coating parameters were used for coating with each of the Eudragit® L 30 D-55 and Eudragit® S 100 aqueous film coatings.

| | |
| --- | --- |
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.8 Bar |
| Pump Rate | 2-6 gram per minute |

47.9.1 Coat Amoxicillin matrix pellets with L30 D-55 dispersim to achieve a 20% coat weight gain.

47.9.2 Coat another batch of Amoxicillin matrix pellets with L30 D-55 dispersion to achieve a 20% weight gain. Coat the L30 D-55 pellets with the Aquacoat Dispersion to achieve a 10% coat weight gain.

47.9.3 Coat Amoxicillin matrix pellets with S100 dispersion to achieve a 37% coat weight gain.

47.10 Preparation of Amoxicillin Granulation for Tabletting

TABLE 19

Composition of Amoxicillin Granulation (Immediate Release)

| Component | Percentage (%) |
|---|---|
| Amoxicillin Trihydrate powder | 92 |
| Avicel PH 101 | 7.0 |
| Hydroxypropyl methylcellulose, NF* | 1.0 |
| Total | 100 |

*Hydroxypropyl methylcellulose was added as a 2.9% w/w aqueous solution during wet massing.

47.10.1 Blend Amoxicillin and Avicel® PH 101 using a low shear blender.
47.10.2 Add the hydroxypropyl methylcellulose binder solution slowly into the powder blend under continuous mixing.
47.10.3 Dry the granulation at 60° C. using a fluid bed dryer until the exhaust temperature reaches 40° C.
47.10.4 Granules between 20 and 40 Mesh are collected for further processing.

47.11 Tabletting of the Amoxicillin Pellets

TABLE 20

Composition of Amoxicillin Tablets

| Component | Percentage (%) |
|---|---|
| Amoxicillin granules | 32.5 |
| Avicel PH 200 | 5.0 |
| Amoxicillin L30D-55 coated pellets | 20 |
| Amoxicillin Aquacoated pellets | 20 |
| Amoxicillin S100 coated pellets | 20 |
| Colloidal silicon dioxide | 1.5 |
| Magnesium stearate | 1.0 |
| Total | 100 |

47.11.1 Blend the Amoxicillin granules, Avicel PH-200, Amoxicillin pellets and colloidal silicon dioxide for 15 minutes in a tumble blender.
47.11.2 Add the magnesium stearate to the blender, and blend for 5 minutes.
47.11.3 Compress the blend on a rotary tablet press.
47.11.4 The fill weight should be adjusted to achieve a 500 mg dose tablet.

Four Pulses

Example 48

Clarithromycin Pellet Formulation and Preparation Procedure 48.1 Pellet Formulation
The composition of the clarithromycin matrix pellets provided in Table 21.

TABLE 21

Composition of Clarithromycin Pellets

| Component | Percentage (%) |
|---|---|
| Clarithromycin | 50.6 |
| Lactose monohydrate, spray dried | 32.1 |
| Silicified microcrystalline cellulose | 14.6 |
| Polyoxyl 35 Castor Oil* | 1.7 |
| Hydroxypropyl methylcellulose* | 1.0 |
| Total | 100 |

*Hydroxypropyl methylcellulose and Polyoxyl 35 were added as an 8.7% w/w aqueous solution during wet massing.

48.2 Preparation Procedure for Clarithromycin Matrix Pellets
48.2.1 Blend clarithromycin, silicified microcrystalline cellulose and lactose monohydrate using a Robot Coupe high shear granulator.
48.2.2 Prepare the binder solution by adding the Polyoxyl to the purified water while stirring. After that is mixed, slowly add the hydroxypropyl methylcellulose and continue to stir until a solution is achieved.
48.2.3 Add binder solution slowly into the powder blend under continuous mixing.
48.2.4 Granulate the powders in the high shear granulator with the binder solution.
48.2.5 Extrude the wet mass using an LCI Bench Top Granulator. The diameter of the screen of the Bench Top Granulator was 1.2 mm.
48.2.6 Spheronize the extrudate using a Model SPH20 Caleva Spheronizer.
48.2.7 Dry the spheronized pellets at 50° C. overnight.
48.2.8 Pellets between 18 and 30 Mesh were collected for further processing.

48.3 Preparation of an Eudragit® L 30 D-55 Aqueous Coating Dispersion
48.3.1 Dispersion Formulation
The composition of the aqueous Eudragit L30D-55 dispersion applied to the clarithromycin matrix pellets is provided below in Table 22.

TABLE 22

Eudragit ® L 30 D-55 Aqueous Coating Dispersion

| Component | Percentage (%) |
|---|---|
| Eudragit ® L 30 D-55 | 40.4 |
| Triethyl Citrate | 1.8 |
| Talc | 6.1 |
| Water | 51.7 |
| Solids Content | 20.0 |
| Polymer Content | 12.1 |

48.4 Preparation Procedure for an Eudragit® L 30 D-55 Aqueous Dispersion
48.4.1 Suspend triethyl citrate and talc in deionized water.
48.4.2 The TEC/talc suspension is then homogenized using a PowerGen 700 high shear mixer.
48.4.3 Add the suspension from 4.2.2 slowly to the Eudragit® L 30 D-55 latex dispersion while stirring.
48.4.4 Allow the coating dispersion to stir for one hour prior to application onto the clarithromycin matrix pellets.

48.5 Preparation of an Eudragit® S 100 Aqueous Coating Dispersion
48.5.1 Dispersion Formulation
The composition of the aqueous Eudragit® S 100 dispersion applied to the clarithromycin matrix pellets is provided below in Table 23.

TABLE 23

| Eudragit ® S 100 Aqueous Coating Dispersion | |
|---|---|
| Component | Percentage (%) |
| Part A | |
| Eudragit ® S 100 | 10.0 |
| 1N Ammonium Hydroxide | 5.1 |
| Triethyl Citrate | 5.0 |
| Water | 64.9 |
| Part B | |
| Talc | 5.0 |
| Water | 10.0 |
| Solid Content | 25.0 |
| Polymer Content | 10.0 |

48.6 Preparation Procedure for an Eudragit® S 100 Aqueous Dispersion

Part A:

48.6.1 Dispense Eudragit® S 100 powder in deionized water with stirring.

48.6.2 Add ammonium hydroxide solution drop-wise into the dispersion with stirring.

48.6.3 Allow the partially neutralized dispersion to stir for 60 minutes 48.6.4 Add the triethyl citrate drop-wise to the dispersion and stir for 60 minutes prior to the addition of Part B.

Part B:

48.6.5 Disperse talc in the required amount of water 48.6.6 Homogenize the dispersion using a PowerGen 700D high shear mixer.

48.6.7 Part B is then added slowly to the polymer dispersion in Part A with a mild stirring.

48.7 Coating Conditions for the Application of Aqueous Coating Dispersions

The following coating parameters were used for coating with each of the Eudragit® L 30 D-55 and Eudragit® S 100 aqueous film coatings.

| | |
|---|---|
| Coating Equipment | STREA 1 ™ Table Top Laboratory Fluid Bed Coater |
| Spray nozzle diameter | 1.0 mm |
| Material Charge | 300 gram |
| Inlet Air Temperature | 40 to 45° C. |
| Outlet Air Temperature | 30 to 33° C. |
| Atomization Air Pressure | 1.6 Bar |
| Pump Rate | 2 gram per minute |

48.7.1 Coat matrix pellets with L30 D-55 dispersion such that you apply 12% coat weight gain to the pellets.

48.7.2 Coat matrix pellets with L30 D-55 dispersion such that you apply 30% coat weight gain to the pellets.

48.7.3 Coat matrix pellets with S100 dispersion such that you apply 37% coat weight gain to the pellets.

48.8 Encapsulation of the Clarithromycin Pellets

Pellets are filled into size 00 hard gelatin capsules at a ratio of 20%:30%:20%:30% Immediate-release matrix pellets (uncoated), L30 D-55 coated pellets 12% weight gain, L30D-55 coated pellets 30% weight gain and S100 coated pellets respectively. The capsule is filled with the four different pellets to achieve a total dose of 250 mg/capsule.

The present invention is particularly advantageous in that there is provided an antibiotic product which provides an improvement over twice a day administration of the antibiotic and an improvement over a once a day administration of the antibiotic.

Numerous modification and variations of the present invention are possible in light of the above teachings and therefore, within the scope of the appended claims the invention may be practiced otherwise than as particularly described.

What is claimed is:

1. A once-a-day amoxicillin product comprising at least two dosage forms, wherein the at least two dosage forms consist of a first amoxicillin dosage form and a second amoxicillin dosage form, wherein each of the first and second amoxicillin dosage forms comprises a pellet or a particle comprising a pharmaceutically active ingredient and a pharmaceutically acceptable carrier, the pharmaceutically active ingredient consisting of amoxicillin, wherein the first amoxicillin dosage form is an immediate release dosage form, the second dosage form is a delayed release dosage form, wherein the pellet or the particle of the second dosage form is coated with a non-pH sensitive delayed release component or an enteric release component, and wherein each of the first and second amoxicillin dosage farms initiates release of amoxicillin at different times and Cmax of the total amoxicillin released from the amoxicillin product is achieved in less than about 12 hours from administration, the once-a-day amoxicillin product contains the total dosage of amoxicillin for a twenty-four hour period.

2. The product of claim 1, wherein the Cmax for the product is reached no earlier than four hours after administration.

3. The product of claim 1, wherein the amoxicillin released from the first dosage form reaches a Cmax within from about 0.5 hours to about hours after administration of the product.

4. The product of claim 1, wherein the amoxicillin released from the second dosage form reaches a Cmax in no more than about 4 hours after administration of the product.

5. The product of claim 1, wherein the product is an oral dosage form.

6. The product of claim 1, wherein the pellet or the particle is formed into a unitary pharmaceutical product.

7. A process for treating a bacterial infection in a host comprising: administering to a host the amoxicillin product of claim 1 once-a-day.

8. A once-a-day amoxicillin product comprising at least two dosage forms, wherein the at least two dosage forms consist of a first amoxicillin dosage form and a second amoxicillin dosage form, wherein each of the first and second amoxicillin dosage forms comprises a pellet or a granule comprising a pharmaceutically active ingredient and a pharmaceutically acceptable carrier, the pharmaceutically active ingredient consisting of amoxicillin, wherein the first amoxicillin dosage form is an immediate release dosage form, the second dosage form is a delayed release dosage form, wherein the pellet or the granule of the second dosage form is coated with a non-pH sensitive delayed release component or an enteric release component, and wherein each of the first and second amoxicillin dosage forms initiates release of amoxicillin at different times and $C_{max}$ of the total amoxicillin released from the amoxicillin product is achieved in less than about 12 hours from administration, the once-a-day amoxicillin product contains the total dosage of amoxicillin for a twenty-four hour period.

9. The product of claim 8, wherein the $C_{max}$ for the product is reached no earlier than four hours after administration.

10. The product of claim 8, wherein the amoxicillin released from the first dosage form reaches a $C_{max}$ within from about 0.5 hours to about 2 hours after administration of the product.

11. The product of claim 8, wherein the amoxicillin released from the second dosage form reaches a $C_{max}$ in no more than about 4 hours after administration of the product.

12. The product of claim 8, wherein the product is an oral dosage form.

13. The product of claim 8, wherein the pellet or the granule is formed into a unitary pharmaceutical product.

* * * * *

UNITED STATES PATENT AND TRADEMARK OFFICE
CERTIFICATE OF CORRECTION

PATENT NO. : 8,889,187 B2  
APPLICATION NO. : 13/273966  
DATED : November 18, 2014  
INVENTOR(S) : Edward M. Rudnic et al.

Page 1 of 1

It is certified that error appears in the above-identified patent and that said Letters Patent is hereby corrected as shown below:

In the Claims

Claim 3, Column 24, line 32, "about hours" should read --about 2 hours--.

Signed and Sealed this
Seventeenth Day of March, 2015

Michelle K. Lee
*Director of the United States Patent and Trademark Office*